(12) United States Patent
Okano et al.

(10) Patent No.: US 8,685,328 B2
(45) Date of Patent: Apr. 1, 2014

(54) METHOD FOR PURIFYING INSIDE OF ROOM

(75) Inventors: Hiroaki Okano, Osaka (JP); Kazuo Nishikawa, Osaka (JP); Hisaharu Yagi, Osaka (JP); Norihiro Matsuoka, Osaka (JP); Tomonori Akai, Osaka (JP); Misaki Nakamura, Osaka (JP); Yoshihiro Shimizu, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 436 days.

(21) Appl. No.: 13/060,700

(22) PCT Filed: May 21, 2009

(86) PCT No.: PCT/JP2009/059330
§ 371 (c)(1),
(2), (4) Date: Feb. 25, 2011

(87) PCT Pub. No.: WO2010/023999
PCT Pub. Date: Mar. 4, 2010

(65) Prior Publication Data
US 2011/0150697 A1  Jun. 23, 2011

(30) Foreign Application Priority Data

Aug. 26, 2008  (JP) .................................. 2008-217355
Jan. 9, 2009   (JP) .................................. 2009-003580

(51) Int. Cl.
*A62B 7/08*    (2006.01)
*A61L 2/00*    (2006.01)
*A61L 9/00*    (2006.01)
*C25B 5/00*    (2006.01)
*H05F 3/00*    (2006.01)

(52) U.S. Cl.
USPC .......... 422/121; 422/1; 422/4; 422/5; 422/22; 422/186.04; 204/156; 204/164

(58) Field of Classification Search
USPC ........... 422/1, 4–5, 22, 121, 186.04; 204/156, 204/164
See application file for complete search history.

(56) References Cited

U.S. PATENT DOCUMENTS

2003/0072675 A1  4/2003  Takeda et al.
2006/0263280 A1  11/2006 Ohtsuka et al.
2007/0109711 A1  5/2007  Sekoguchi et al.

FOREIGN PATENT DOCUMENTS

JP  2002-95731 A   4/2002
JP  2004-33875 A   2/2004
(Continued)

OTHER PUBLICATIONS

Japanese Patent Office English Translation of the "Detailed Description" section of JP 2004-363088.*

(Continued)

*Primary Examiner* — Monzer R Chorbaji
(74) *Attorney, Agent, or Firm* — Birch, Stewart, Kolasch & Birch, LLP

(57) ABSTRACT

In order to remove a pathogenic effect of a microorganism in a room or a work space in a short period of time, an ion diffusing apparatus, which includes an ion generator (17, 18) for generating positive ions each including $H^+(H_2O)_m$ and negative ions each including $O_2^-(H_2O)_n$, where m and n are arbitrary integers, and a blower for delivering the positive ions and the negative ions, which are generated from the ion generator (17), from a blowout opening, is operated to widely distribute, with a high concentration, the positive ions and the negative ions in the room.

7 Claims, 30 Drawing Sheets

(56) References Cited

FOREIGN PATENT DOCUMENTS

| JP | 2004-251497 | A | | 9/2004 |
|---|---|---|---|---|
| JP | 2004-293893 | A | | 10/2004 |
| JP | 2004-363088 | | * | 12/2004 |
| JP | 2004-363088 | A | | 12/2004 |
| JP | 3797993 | B2 | | 7/2006 |
| RU | 2 089 073 | C1 | | 5/1995 |

OTHER PUBLICATIONS

English abstract only of RU 2241492 C2 dated Dec. 10, 2004.

* cited by examiner

● : MEASUREMENT POINT
(HEIGHT: 2.5 m)

FIG.21

| MEASUREMENT POINT | (+) IONS (PER cm³) | (−) IONS (PER cm³) | STERILIZATION IONS (PER cm³) |
|---|---|---|---|
| A1 | 49,000 | 47,000 | 47,000 |
| A3 | 300,000 | 340,000 | 63,500 |
| A5 | 80,000 | 90,000 | 80,000 |
| C1 | 32,000 | 34,000 | 32,000 |
| C3 | 15,000 | 18,000 | 15,000 |
| C5 | 47,000 | 57,000 | 47,000 |
| E1 | 18,000 | 18,000 | 18,000 |
| E3 | 27,000 | 33,000 | 27,000 |
| E5 | 27,000 | 30,000 | 27,000 |
| AVERAGE NUMBER OF MEASUREMENT POINTS | 66,111 | 74,111 | 39,611 |
| GROWTH RATE% | | | 154 |

NOTE THAT MEASUREMENT POINT A3 IS AVERAGE VALUE OF A1 AND A5

FIG.25

| | CONCENTRATION OF IONS (PER cm³) | EFFECTS AND EFFICACIES | | | | |
|---|---|---|---|---|---|---|
| | | REMOVAL OF AIRBORNE VIRUSES | REMOVAL OF BACTERIA | REMOVAL OF MOLD SPORES | REMOVAL OF AIRBORNE MITE ALLERGENS | REMOVAL OF ABSORBED ODORS |
| 1 | 100,000 IONS | | | | | • TIME PERIOD REQUIRED FOR MAKING INTENSITY OF ABSORBED SWEAT ODORS (ISOVALERIC ACID) ONE LEVEL DOWN → 4 HOURS |
| 2 | 50,000 IONS | • REMOVAL RATE OF HUMAN INFLUENZA A VIRUSES (SUBTYPE H1N1) IN 10 MINUTES IS 96.102% (REMOVAL RATE WITH 1-m³-CHAMBER TEST IN 25 MINUTES IS 99.97%)<br>• REMOVAL RATE OF AVIAN INFLUENZA A VIRUSES IS 99.9% IN 10 MINUTES (SUBTYPE H5N1) | REMOVAL OF ADHERING BACTERIA (STAPHYLOCOCCUS AUREUS AND ESCHERICHIA COLI) IS 99% (TEST RESULTS IN REFRIGERATOR: EXPOSED FOR 7 DAYS) | • GROWTH OF ADHERING MOLD (CLADOSPORIUM) IS INHIBITED (HYPHAL GROWTH IS INCONSPICUOUS: 25% OR SMALLER OF TEST A

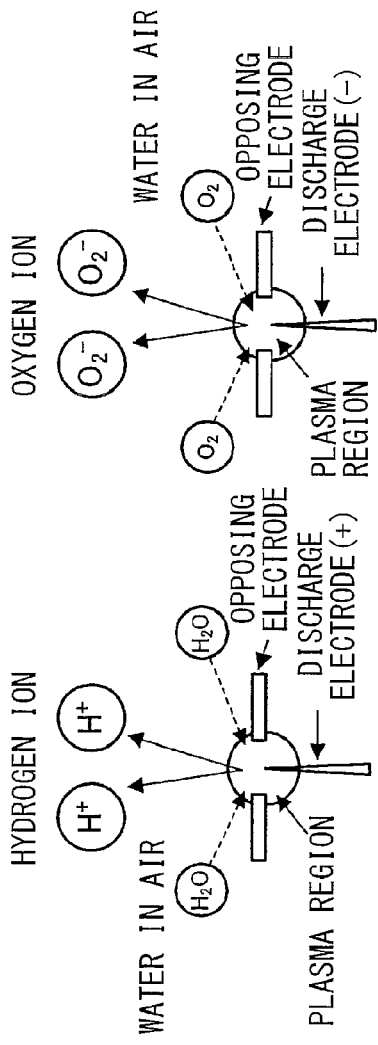
FIG.26

FIG.27

MECHANISM FOR INACTIVATING AIRBORNE VIRUSES

POSITIVE AND NEGATIVE IONS SURROUND SURFACE OF AIRBORNE VIRUS

METHOD FOR PURIFYING INSIDE OF ROOM

BACKGROUND OF THE INVENTION

1. Field of the Invention

The present invention relates to a method of purifying an inside of a room, in which positive ions and negative ions are used against such microorganisms (in particular, pathogenic microorganisms) as viruses, bacteria, fungi, and various allergens, which are suspended in air or adhering to a wall or the like in a person's room or work space and a breeding room for livestock or the like, to thereby remove pathogenic effects of those microorganisms.

2. Description of the Related Art

In recent years, a technology of purifying air in a room by emitting positive ions and negative ions to the room has grown in use (see Patent Literature 1). For example, in anion diffusing apparatus described in Patent Literature 1, an ion generator for generating positive ions and negative ions is disposed in the middle of an air path for releasing air currents to a space to be purified, thereby emitting positive ions and negative ions to the outside space.

The ions emitted to the outside cause airborne bacteria to be killed and viruses to be inactivated, and hence the air in the entire room can be purified.

CITATION LIST

Patent Literature

[PTL 1] JP 3797993 B2

SUMMARY OF INVENTION

Technical Problem

In conventional apparatuses provided with an ion generator, a space purifying function utilizing positive ions and negative ions is merely a supplemental function that follows such essential functions of an air purifier and an air conditioner as removing dust and odors in a room by a filter, and appropriately adjusting temperature and humidity in a room. In other words, those conventional products have not been developed with emphasis on the function of positive ions and negative ions.

For example, in the case of an apparatus provided with an ion generator for generating positive ions and negative ions, even when a room is as small as about 6 to 8 tatami mats, the concentration of ions in the air in the room is about 2,000 per $cm^3$ to 3,000 per $cm^3$ on average, and, even in the case of airborne bacteria, only 90% thereof can be killed in a one-pass test. Accordingly, in the case of virulent viruses typified by new avian influenza and human influenza, which emerge with adaptations of viruses, there is a fear that before the air purifier or the air conditioner removes those virulent viruses, the viruses are transmitted to people in the same room space.

Here, a person generally breathes in a volume of approximately 500 $cm^3$ of air in one breath during rest. This amount of air is extremely small compared to a space volume of the room. In view of this, it conceivably takes at least a few minutes for viruses spread around in a room by a person's cough or sneeze to be transmitted to another person in the room through breathing in. Accordingly, a level practical for prevention of virus infection may be to inactivate 99% or more of the viruses in about 10 minutes after the viruses are spread.

For example, in the case of norovirus, it is said that the infection becomes established with the inoculation of about 100 viruses. Assuming that there are 10,000 viruses in a room, even if 99% of the viruses are removed, this leaves 100 viruses, and thus there still remains a risk of infection. However, if 99.9% of the viruses are removed in a short period of time, the remaining viruses are only 10, which therefore results in a significantly reduced probability of infection. In summary, it can be understood that, in the world of viruses, even though a difference is merely 0.9%, there is a significant gap between a removal rate of 99% and a removal rate of 99.9% in terms of the probability of infection.

Of course, it is possible to kill/remove 100% of viruses or bacteria with chemicals. However, there has existed no method that, without adversely affecting human bodies in a room, acts on such virulent viruses or bacteria (in particular, pathogenic microorganisms) and kills/removes those viruses and bacteria in a short period of time, to thereby prevent infection to human bodies at a high level.

Note that, in this description, the microorganisms include viruses, bacteria, molds, and allergens that trigger allergic reactions in human bodies. Then, in a case where the microorganism causes an inconvenient effect, such as a disease, to a human body, this kind of microorganism is referred to as pathogenic microorganism. Further, the inconvenient effect that the microorganism causes to a human body is referred to as pathogenic effect, and elimination of the pathogenic effect is referred to as removal. Therefore, inactivation of viruses, killing of bacteria and molds, modifying allergens to eliminate effects thereof, and the like correspond to the removal of pathogenic effects of the microorganisms.

In order to achieve the above-mentioned object, the present invention has been made, and thus provides a method of purifying an inside of a room which is capable of removing a pathogenic effect of a microorganism in a room in a short period of time.

Solution to Problem

In order to achieve the above-mentioned object, according to the present invention, there is provided a method of purifying an inside of a room, including operating an ion diffusing apparatus including an ion generator for generating positive ions each including $H^+(H_2O)_m$ and negative ions each including $O_2^-(H_2O)_n$, where m and n are arbitrary integers, and a blower for delivering the positive ions and the negative ions, which are generated from the ion generator, from a blowout opening, to widely distribute, with a high concentration, the positive ions and the negative ions in a room or a work space, whereby a pathogenic effect is removed from an airborne microorganism and/or an adhering microorganism.

Further, according to the present invention, in the method of purifying an inside of a room, a concentration of the positive ions and the negative ions in air of the inside of the room is set to 7,000 per $cm^3$ or higher. With this, it is possible to remove the pathogenic effects of the airborne viruses by 99% or higher in a short period of time.

Further, according to the present invention, in the method of purifying an inside of a room, a concentration of the positive ions and the negative ions in air of the inside of the room is set to 30,000 per $cm^3$ or higher. With this, it is possible to inhibit the growth of adhering mold spores.

Further, according to the present invention, in the method of purifying an inside of a room, a concentration of the positive ions and the negative ions in air of the inside of the room is set to 50,000 per $cm^3$ or higher. With this, it is possible to remove the pathogenic effects of the airborne viruses by 99.9% or higher in a short period of time, and it is also possible to remove the pathogenic effects of the adhering bacteria by 99% or higher.

Further, according to the present invention, in the method of purifying an inside of a room, a duct connecting between the blowout opening and the blower is included, the ion generator includes: a positive ion generation portion for generating the positive ions; and a negative ion generation portion for generating the negative ions, the blast duct is provided with a flow aligning portion for aligning air flowing through the duct upstream of the ion generator, and the positive ion generation portion and the negative ion generation portion are disposed so as to be spaced apart from each other in a direction intersecting a flow direction.

With this, two areas extending in the flow direction, that is, an area in which only the positive ions generated from the positive-ion generation portion flow and an area in which only the negative ions generated from the negative ion generation portion flow, are formed while being spaced apart from each other in the direction intersecting the flow direction. Therefore, ion loss caused by neutralization of positive ions and negative ions can be prevented, thereby enabling positive ions and negative ions to be diffused in large quantity in the room.

Further, according to the present invention, in the method of purifying an inside of a room, a sectioning portion for sectioning between the positive ion generation portion and the negative ion generation portion along an air current is provided.

With this, the two areas formed to extend in a direction of air currents flowing through a blast duct, that is, the area in which only the positive ions flow and the area in which only the negative ions flow, are sectioned by the sectioning portion. Therefore, the ion loss caused by the neutralization of positive ions and negative ions can be reliably prevented, thereby enabling positive ions and negative ions to be diffused efficiently in large quantity in the room.

Further, according to the present invention, in the method of purifying an inside of a room, a generation amount of the positive ions generated from the positive ion generation portion and a generation amount of the negative ions generated from the negative ion generation portion are each 1.5 million per $cm^3$ or higher at a position distanced 50 cm from the positive ion generation portion and the negative ion generation portion.

With this, positive ions and negative ions are constantly generated from the ion generator in abundance, thereby enabling positive ions and negative ions to be easily distributed in the room with a high concentration.

Further, according to the present invention, the method of purifying an inside of a room further includes delivering an air current from the blowout opening in a substantially horizontal direction so that an upper portion of the air current flows with a higher blowout speed compared to a blowout speed of a lower portion of the air current.

With this, an air current blown out from the upper portion of the blowout opening at high speed serves as an air curtain, and ions contained in a slow air current in the lower portion are supplied to a lower portion of the room. Therefore, the ions are prevented from being diffused upward by the air curtain, thereby enabling ions to be widely distributed in a space in the room below a certain height from a floor surface (for example, approximate height of a person) with the above-mentioned ion concentration of 10,000 per $cm^3$.

Advantageous Effects of Invention

According to the present invention, it is possible to remove the pathogenic effect of the microorganism in a short period of time in the room. Therefore, the present invention helps prevent infection caused by the pathogenic microorganisms in the room.

BRIEF DESCRIPTION OF DRAWINGS

[FIG. 21] Data indicating results of measurement on an amount of ions in air for respective measurement points of FIG. 20.

[FIG. 25] A table showing effects and efficacies that are newly realizable by a technology of the present invention in which positive ions and negative ions are distributed in a room with a high concentration.

[FIG. 26] An explanatory diagram of a mechanism for generating positive ions and negative ions.

[FIG. 27] An explanatory diagram of a mechanism in which positive ions and negative ions inactivate an airborne virus.

[FIG. 28] An explanatory diagram of a test method and a device, with which a reduction effect against infectivity of avian influenza A viruses subtype H5N1 to cells was examined after positive ions and negative ions were applied.

[FIG. 31] An explanatory diagram of a test method and a device, with which a reduction effect against infectivity of influenza A viruses subtype H3N2 to chicks was examined after positive ions and negative ions were applied.

DETAILED DESCRIPTION OF THE INVENTION

Hereinbelow, representative embodiments of the present invention are described with reference to the drawings.

<First Embodiment>

Figure 1:
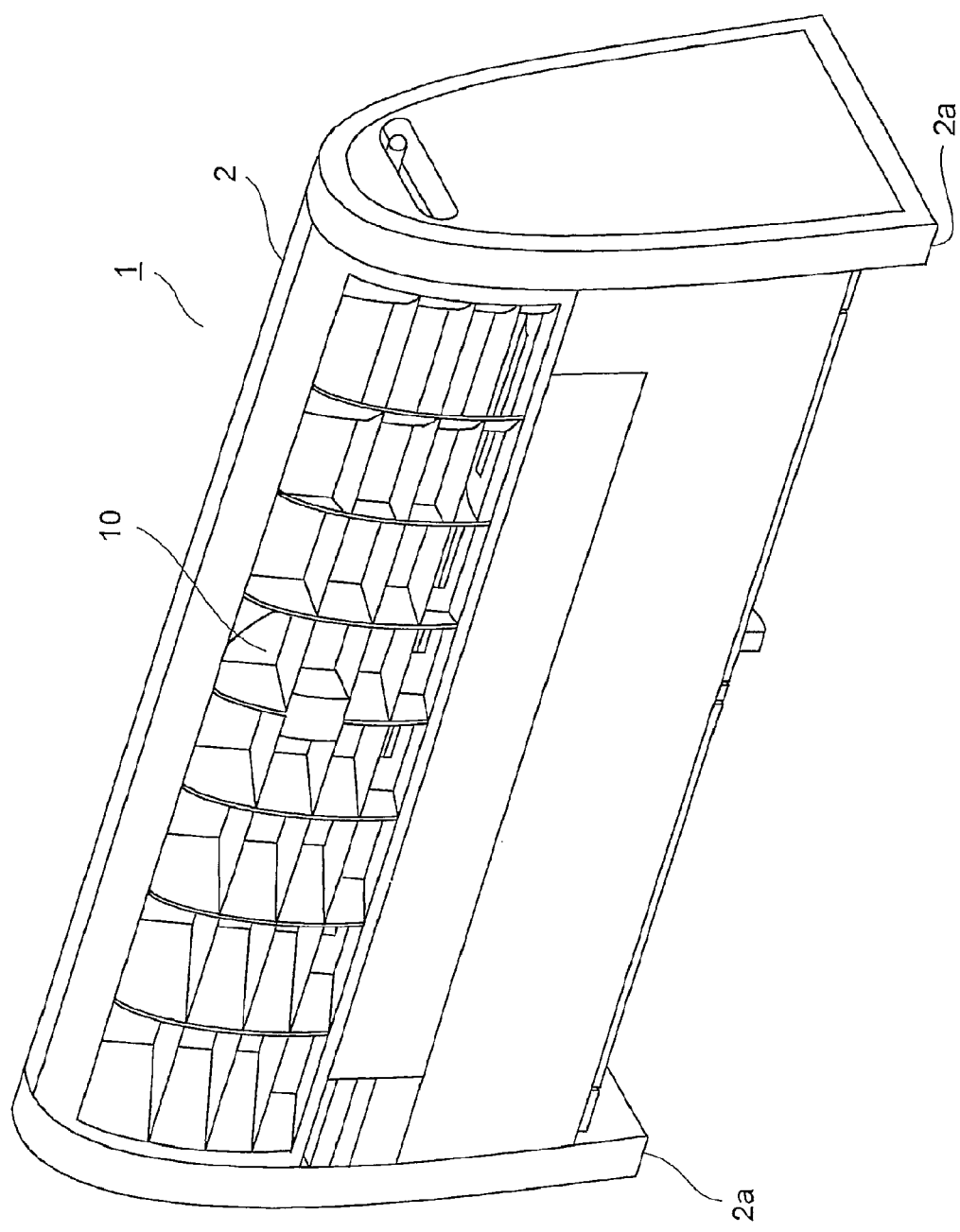
[FIG. 1] A perspective view illustrating an ion diffusing apparatus according to a first embodiment of the present invention.

FIG. 1 is an external perspective view illustrating an ion diffusing apparatus according to a first embodiment. An ion diffusing apparatus 1 has leg portions 2a provided to left and right ends of a housing 2, and is placed on a floor surface of a room. A blowout opening 10 is provided to a front upper portion of the housing 2.

Figure 2:
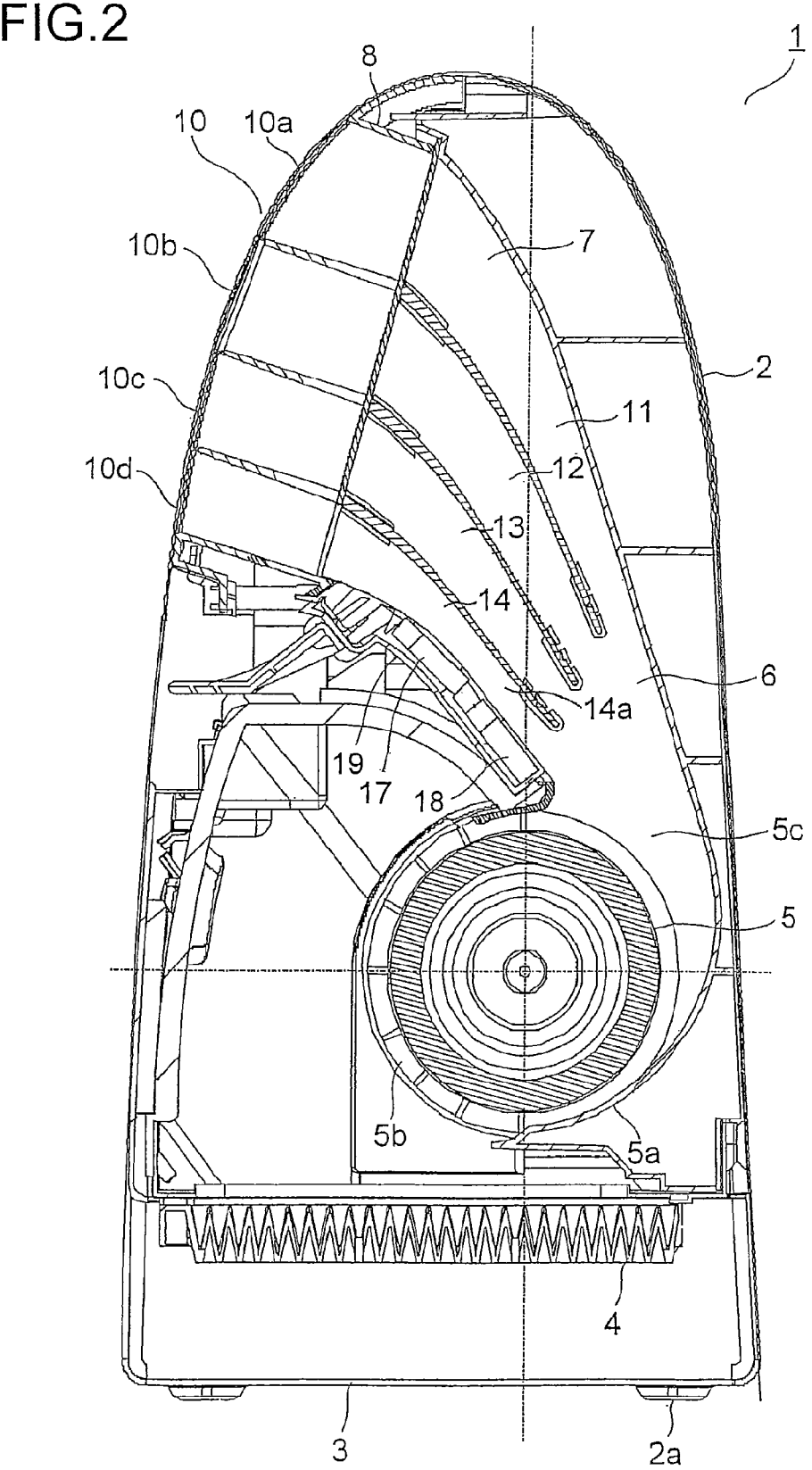
[FIG. 2] A side sectional view illustrating the ion diffusing apparatus according to the first embodiment of the present invention.

FIG. 2 is a side sectional view of the ion diffusing apparatus 1. A bottom surface of the housing 2 is provided with a suction opening 3 for sucking in air in the room. A blower 5, which is covered with a housing 5a, is disposed in a lower portion of the housing 2. The blower 5 includes a cross-flow fan, which is rotationally driven at a predetermined rpm, and draws air from an air inlet 5b into the housing 5a from a circumferential direction of rotor blades (not shown) while discharging air from an air outlet 5c in the circumferential direction of the rotor blades. An air filter 4 is provided between the suction opening 3 and the blower 5.

The air outlet 5c of the blower 5 is connected to the blowout opening 10 by a duct 6, through which an air current from the blower 5 flows. The duct 6, which is integrally formed with the housing 5a, extends upward while bending forward, as illustrated in the figure. The duct 6 is separated in a vertical direction into a plurality of vertically-separated paths 11, 12, 13, and 14 in the stated order from the top. Hereinbelow, the direction of air currents flowing through the vertically-separated paths 11 to 14 of the duct 6 is referred to as "flow direction (direction of arrow A of FIG. 5)", whereas a direction intersecting such a direction as described above is referred to as "direction intersecting the flow direction (direction of arrow B of FIG. 5)".

The vertically-separated path 11 positioned above is disposed on an outer circumference side of the blower 5, and the vertically-separated path 14 positioned below is disposed on an inner circumference side of the blower 5. The blowout opening 10 is vertically separated corresponding to the respective vertically-separated paths 11 to 14, thereby forming opening portions 10a, 10b, 10c, and 10d. Each of the vertically-separated paths 11 to 14 is provided with a vertical-widening portion 7 and a lateral-widening portion 8 on an upstream side and on a downstream side, respectively, details of which are described later. A lower wall of the vertically-separated path 14 is provided with notches (not shown) so as to expose an upper surface of a holding member 19, which is provided with ion generation portions 17A and 17B of a first ion generator 17 and ion generation portions 18A and 18B of a second ion generator 18 (see FIG. 3).

Figure 3A:
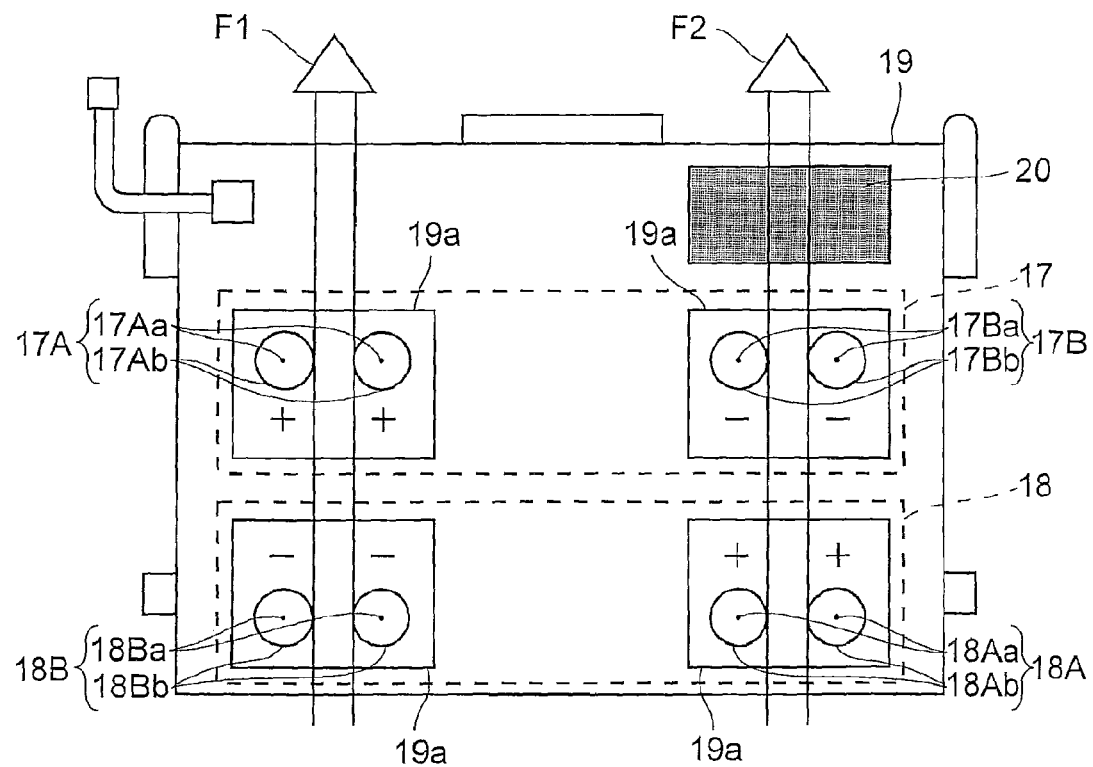
[FIG. 3] A plan view (FIG. 3(a)) and a side view (FIG. 3(b)) illustrating structure of ion generators of the ion diffusing apparatus according to the first embodiment of the present invention.
Figure 3B:
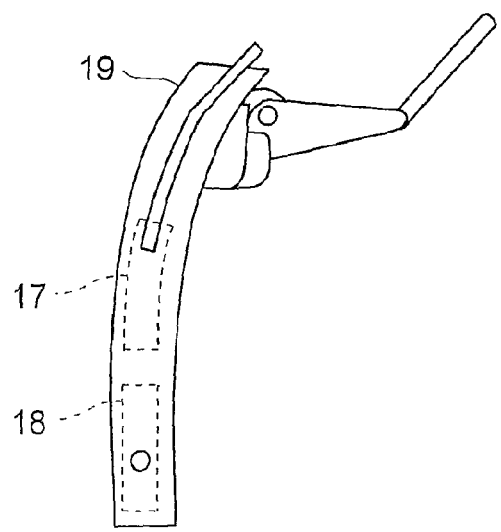

FIG. 3 is a plan view illustrating structure of the ion generators according to this embodiment. The ion generators 17 and 18 include: a pair of the ion generation portions 17A and 17B spaced apart from each other in the direction intersecting the flow direction and a pair of the ion generation portions 18A and 18B spaced apart from each other in the direction intersecting the flow direction; a power feeding portion (not shown) for applying voltage to the ion generation portions 17A, 17B, 18A, and 18B; and the holding member 19 for holding the ion generation portions 17A, 17B, 18A, and 18B and the power feeding portion. When the power feeding portion applies voltage to the ion generation portions 17A, 17B, 18A, and 18B, the ion generation portions 17A and 17B perform corona discharge, to thereby generate ions.

The ion generation portions 17A and 17B include discharge electrode projecting portions 17Aa and 17Ba having a sharp pointed shape, and induction electrode rings 17Ab and 17Bb respectively surrounding the discharge electrode projecting portions 17Aa and 17Ba, and the discharge electrode projecting portions 17Aa and 17Ba are disposed in center portions of the induction electrode rings 17Ab and 17Bb, respectively. The ion generation portion 17A generates positive ions, whereas the ion generation portion 17B generates negative ions. The same applies to the ion generation portions 18A and 18B of the second ion generator 18. Thus, the ion generation portion 18A generates positive ions, whereas the ion generation portion 18B generates negative ions. Note that, an ion sensor 20 for detecting an abnormality in ion generation amount is disposed downstream of the ion generation portion 17B in the flow direction.

The first ion generator 17 and the second ion generator 18 are mounted on the lower wall of the vertically-separated path 14, and the pair of the ion generation portions 17A and 17B and the pair of the ion generation portion 18A and 18B are respectively disposed at positions intersecting the flow direction in which air flows.

The ion generators 17 and 18 mounted to the lower wall of the vertically-separated path 14 are of cartridge type, and are both held by a single holding member 19. Replacement of the cartridge is performed when the ion sensor 20 has detected an abnormality in ion generation amount or when a predetermined replacement date has been reached. The pair of the ion generators 17 and 18 are spaced apart from each other in the flow direction, and are disposed in parallel such that the polarities of the facing ion generation portions are opposite to each other. In a state in which the cartridge is mounted, the upper surface of the holding member 19 is positioned at the notches of the lower wall of the lowermost vertically-separated path 14, which allows the ion generation portions 17A, 17B, 18A, and 18B of the first ion generator 17 and the second ion generator 18 to be exposed to an inside of the vertically-separated path 14. The upper surface of the holding member 19 is curved along the flow direction, and four positions thereof corresponding to the ion generation portions 17A, 17B, 18A, and 18B each have an opening 19a.

Note that, in this embodiment, description is given of a case in which the holding member 19 holds two ion generators, but structure in which three or more ion generators are held may be employed, thereby increasing the number of ion generators disposed in parallel while being spaced apart from each other in the flow direction.

FIG. 26 is an explanatory diagram of a mechanism for generating positive ions and negative ions. A positive voltage is applied to the ion generation portions 17A and 18A, where water molecules in the air are electrically decomposed in plasma regions created by electric discharge, and hydrogen ions $H^+$ are mainly generated. Then, water molecules in the air aggregate around the generated hydrogen ion, thereby forming a stable, positively-charged cluster ion $H^+(H_2O)_m$. A negative voltage is applied to the ion generation portions 17B and 18B, where oxygen molecules in the air are electrically decomposed in plasma regions created by electric discharge, and oxygen ions $O_2^-$ are mainly generated. Then, water molecules in the air aggregate around the generated oxygen ion, thereby forming a stable, negatively-charged cluster ion $O_2^-(H_2O)_n$. Here, m and n are arbitrary integers. In this description, the "positive ion" refers to a positive cluster ion, whereas the "negative ion" refers to a negative cluster ion. Note that, generation of positive and negative cluster ions has been validated by time-of-flight mass spectrometry.

FIG. 27 is an explanatory diagram of a mechanism in which positive ions and negative ions inactivate an airborne virus. Positive ions and negative ions are simultaneously emitted into the air, and then aggregate around the surface of an airborne microorganism to surround the microorganism. Then, positive ions and negative ions combine to each other instantaneously and generate, on the surface of the microorganism, [.OH] (hydroxyl radicals) and $H_2O_2$ (hydrogen peroxide) in an aggregating manner, which are active species having extremely high oxidation power. Consequently, proteins on the surface of the microorganism are decomposed through chemical reaction, resulting in suppression of activity of the microorganism. In addition, the hydroxyl radical and hydrogen peroxide generated as described above are known to have the property of decomposing odor components in the air. Thus, by generating positive ions and negative ions and then discharging those ions from the blowout opening 10, it is possible to inactivate airborne viruses, kill bacteria and mold, or remove odors in the room.

Note that, as described later, it has been confirmed that the above-mentioned action of positive ions and negative ions produces a higher effect as the concentration of ions in the air is increased. For example, it has been demonstrated that reduction in infectivity of avian influenza A viruses (H5N1) in about 10 minutes is 99% when the concentration of ions in the air is approximately 7,000 per $cm^3$, and is improved to 99.9% when the concentration of ions is increased to 50,000 per $cm^3$ or higher. Further, it has been found for the first time that when the concentration of ions is approximately 30,000 per $cm^3$ or higher, the growth of adhering mold spores can be inhibited. As for the above-mentioned ion generators 17 and 18, a generation amount of positive ions and negative ions from a single ion generator is approximately 1.5 million per $cm^3$ when measured at a position distanced 50 cm from the ion generation portion (approximately 4.8 million per $cm^3$ at a position distanced 25 cm), which is an extremely large number, and hence the ion generators 17 and 18 are devices suitable for maintaining the concentration of ions in the room to such an effective concentration as described above.

Figure 4:
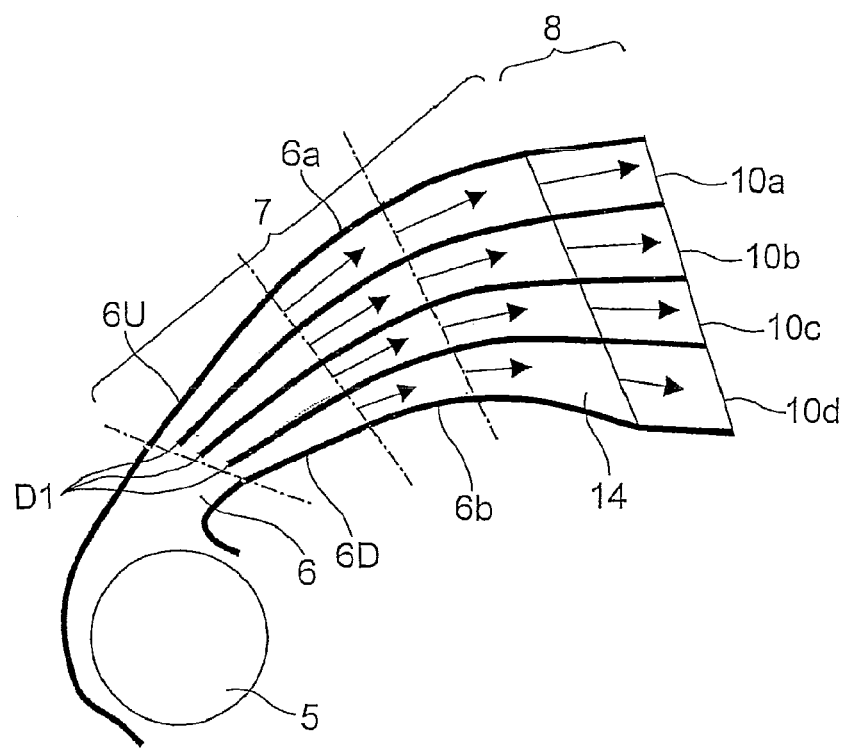
[FIG. 4] A side sectional view illustrating a duct of the ion diffusing apparatus according to the first embodiment of the present invention.

FIG. 4 is a side sectional view illustrating schematic structure of the duct 6. An upper wall 6U and a lower wall 6D of the duct 6 include curved surface portions 6a and 6b, respectively. Respective wall surfaces forming the vertically-separated paths 11 to 14 are curved along the upper wall 6U and the lower wall 6D, and ends D1 thereof are positioned in the vicinity of the blower 5. With this, the vertically-separated paths 11 to 14 are formed to extend from the vicinity of the blower 5 to the blowout opening 10.

Referring to FIG. 4, in the vertical-widening portion 7, a space between the upper wall 6U and the lower wall 6D of the duct 6 is made wider in the vertical direction on the downstream side than on the upstream side. With this, the air current is spread in the vertical direction before being delivered from the blowout opening 10. Each of the vertically-separated paths 11 to 14 is made wider in the vertical direction on the downstream side than on the upstream side, having a cross section of a flow path formed in a slit shape in which a width in the lateral direction is sufficiently large compared to a width in a height direction. For this reason, upper and lower wall surfaces of the respective vertically-separated paths 11 to 14 have larger areas brought into contact with air currents flowing through the duct 6. Owing to this, it is possible to spread in the vertical direction the air currents flowing through the vertically-separated paths 11 to 14 without causing the air currents to flow away from the upper and lower wall surfaces.

Figure 5:
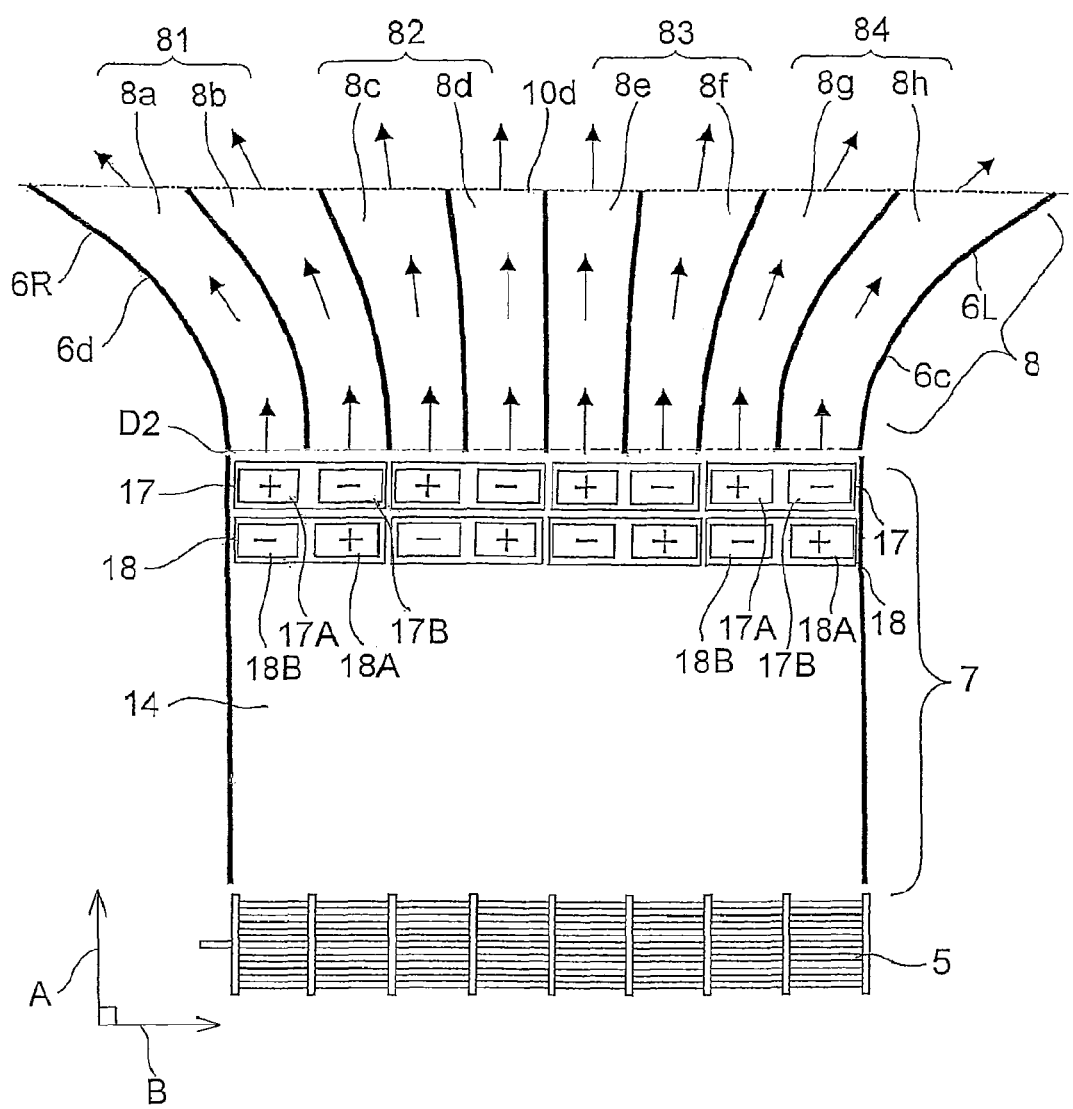
[FIG. 5] A plan view illustrating a lateral-widening portion of the duct of the ion diffusing apparatus according to the first embodiment of the present invention.

The lateral-widening portion 8 is positioned downstream of the vertical-widening portion 7, and has upper and lower wall surfaces thereof extended in a planar manner from the edge of the vertical-widening portion 7. FIG. 5 is a plan view of the lowermost vertically-separated path 14. In the lateral-widening portion 8, a space between a left wall 6L and a right wall 6R of the duct 6 is made wider in the lateral direction on the downstream side than on the upstream side. With this, the air current is spread in the lateral direction before being delivered from the blowout opening 10.

The lateral-widening portion 8 includes laterally-separated paths 8a to 8h constituted of eight narrow paths obtained by separating each of the vertically-separated paths 11 to 14 further in the lateral direction. Now, the lateral-widening portion 8 is conceptually separated into four pairs of paths in the direction intersecting the flow direction by pairing two adjacent laterally-separated paths. Specifically, there are conceptually provided a first path pair 81 including laterally-separated paths 8a and 8b, a second path pair 82 including laterally-separated paths 8c and 8d, a third path pair 83 including laterally-separated paths 8e and 8f, and a fourth path pair 84 including laterally-separated paths 8g and 8h.

In association with the four path pairs, four cartridges each having a single holding member 19 holding the pair of the ion generators 17 and 18 are mounted side by side in the direction intersecting the flow direction. With this, for each of the path pairs, the first ion generator 17 and the second ion generator 18, which are spaced apart from each other in the flow direction, are disposed such that the polarities (polarities of ions generated) of the facing ion generation portions 17A and 18B and the polarities of the facing ion generation portions 17B and 18A are respectively opposite to each other. Further, the first ion generator 17 and the second ion generator 18 are disposed in parallel such that the first ion generator 17 is on the downstream side and the second ion generator 18 is on the upstream side in the flow direction.

Upstream ends D2 of respective wall surfaces forming the laterally-separated paths 8a to 8h are located slightly downstream of the first ion generator 17 in the flow direction, and is positioned in such a manner as to section, on an ion generation portion basis, between the ion generators disposed in the direction intersecting the flow direction and between the ion generation portions of each of the ion generators. Specifically, the positive-ion generation portion 17A of the first ion generator 17 and the negative-ion generation portion 18B of the second ion generator 18 are positioned in the vicinity of an air current inlet of one laterally-separated path (8a, 8c, 8e, or 8g) of each of the path pairs 81, 82, 83, and 84, whereas the negative-ion generation portion 17B of the first ion generator 17 and the positive-ion generation portion 18A of the second ion generator 18 are positioned in the vicinity of an air current inlet of the other laterally-separated path (8b, 8d, 8f, or 8h) of each of the path pairs 81, 82, 83, and 84.

With this path structure of the lateral-widening portion 8, positive ions generated from the positive-ion generation portion 17A of the first ion generator 17 or/and negative ions generated from the negative-ion generation portion 18B of the second ion generator 18 are caused to flow through the one laterally-separated path (8a, 8c, 8e, or 8g) of each of the path pairs 81, 82, 83, and 84, whereas negative ions generated from the negative-ion generation portion 17B of the first ion generator 17 or/and positive ions generated from the positive-ion generation portion 18A of the second ion generator 18 are caused to flow through the other laterally-separated path (8b, 8d, 8f, or 8h) of each of the path pairs 81, 82, 83, and 84. In other words, a dedicated laterally-separated path can be allocated as a flow path for ions generated from each ion generation portion. With this, positive ions and negative ions can be delivered from the blowout opening 10 efficiently and evenly.

Note that, the upstream ends D2 of the respective wall surfaces forming the laterally-separated paths 8a to 8h may be extended so as to pass through between the ion generators 17 and 17 disposed side by side in the direction intersecting the flow direction and between the ion generation portions of each of the ion generators, thereby allowing the ion generation portions 17A, 17B, 18A, and 18B to be positioned inside the laterally-separated paths.

Note that, in this embodiment, as illustrated in FIG. 1, description has been given of the case in which the downstream sides of all the vertically-separated paths 11 to 14 are structured to be divided into the laterally-separated paths 8a to 8h, but the laterally-separated paths 8a to 8h may be provided only to the downstream side of the lowermost vertically-separated path 14 through which positive ions and negative ions flow.

The left wall 6L and the right wall 6R of the duct 6 include curved surface portions 6c and 6d, respectively. The respective wall surfaces forming the laterally-separated paths 8a to 8h are curved along the left wall 6L and the right wall 6R. Each of the laterally-separated paths 8a to 8h is made wider in the lateral direction on the downstream side than on the upstream side by the left and right wall surfaces thereof, and a cross section of a flow path has a width thereof in the lateral direction narrowed compared to the vertical-widening portion 7. With this, the wetted perimeter of the flow path cross section increases, and the left and right wall surfaces of the laterally-separated paths 8a to 8h have larger areas brought into contact with air currents flowing through the duct 6. Accordingly, it is possible to spread in the lateral direction the air currents flowing through the laterally-separated paths 8a to 8h without causing the air currents to flow away from the left and right wall surfaces.

In the ion diffusing apparatus 1 structured as described above, when the blower 5 and the ion generators 17 and 18 are driven, air in the room is taken into the housing 2 from the suction opening 3. The air taken into the housing 2 has dust particles therein collected by the air filter 4, and is then introduced to the blower 5 from the air inlet 5b.

The air discharged from the blower 5 passes through the air outlet 5c, thereby flowing through the duct 6. The air current flowing through the duct 6 is divided to flow into the vertically-separated paths 11 to 14, and the flow path is spread in the vertical direction in the vertical-widening portion 7 while the flow path is widened in the lateral direction in the lateral-widening portion 8. With this, air currents spread in the vertical and lateral directions are delivered from the blowout opening 10.

The air current flowing through the vertically-separated path 14 positioned in the lower portion of the duct 6 is divided into the plurality of laterally-separated paths 8a to 8h. The laterally-separated paths 8a, 8c, 8e, and 8g contain positive ions generated from the ion generation portion 17A of the first ion generator 17 or/and negative ions generated from the ion generation portion 18B of the second ion generator 18. The laterally-separated paths 8b, 8d, 8f, and 8h contain negative ions generated from the ion generation portion 17B of the first ion generator 17 or/and positive ions generated from the ion generation portion 18A of the second ion generator 18. With this, air currents containing positive ions and negative ions are delivered from the opening portion 10d.

Further, air currents to be delivered from the opening portions 10a, 10b, and 10c flow through the vertically-separated paths 11, 12, and 13 positioned in the upper portion of the duct 6, and have high wind speed. Owing to this, the air currents delivered from the opening portions 10a, 10b, and 10c serve as an air curtain to prevent ions from diffusing upward. In this manner, by delivering an air current from the opening portion 10d toward a lower side of the room and delivering air currents from the opening portions 10a, 10b, and 10c toward an upper side of the room, a sufficient amount of ions are supplied to the room, thereby obtaining a high bactericidal effect and a high virus inactivation effect.

Further, the vertically-separated paths 11 to 14 are disposed in the stated order from the top, and the air currents delivered from the opening portions 10a to 10d have wind speeds thereof made weaker in descending order from the top. With this, it is possible to reduce turbulence of air currents.

Figure 6:
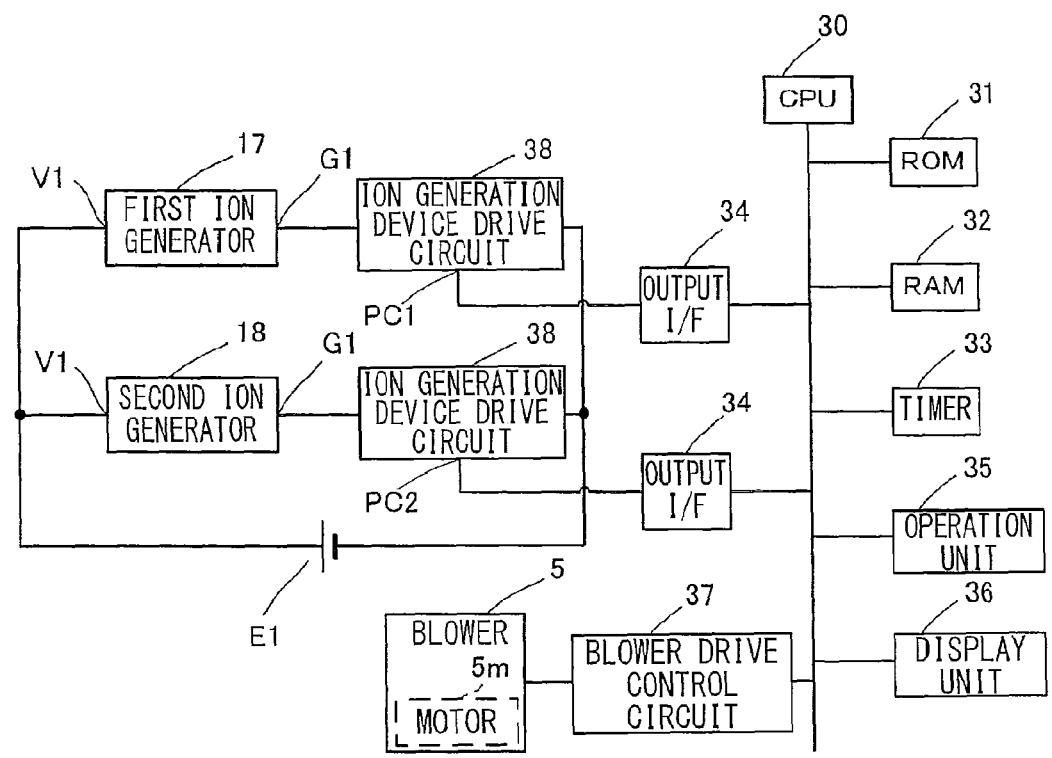
[FIG. 6] A block diagram illustrating a schematic configuration of a control system of the ion diffusing apparatus according to the first embodiment of the present invention.

FIG. 6 is a block diagram illustrating a schematic configuration of a control system of the ion diffusing apparatus 1. A CPU 30 has a central role in the control system, and is connected, by bus connection, to a ROM 31 storing such information as a program, to a RAM 32 for storing information that is generated temporarily, and to a timer 33 for counting time. The CPU 30 executes input/output processing, arithmetic processing, and other processing according to control programs stored in advance in the ROM 31.

The CPU 30 is further connected, by the bus connection, to an operation unit 35 for receiving such an operation as driving or stopping of the ion diffusing apparatus 1, to a display unit 36 including an LCD for displaying such information as an operation content and a driving state, and a blower drive control circuit 37 for driving a motor 5*m* of the blower 5.

Output sides of output interfaces 34 connected to the CPU 30 by the bus connection are respectively connected to control inputs PC1 and PC2 of ion generator drive circuits 38. One output terminal of each of the ion generator drive circuits 38 is connected to a cathode of a DC power supply E1 having an anode thereof connected to a power supply input V1 of the first ion generator 17 and a power supply input V2 of the second ion generator 18, whereas the other output terminals of the ion generator drive circuits 38 are connected to a ground input G1 of the first ion generator 17 and a ground input G2 of the second ion generator 18, respectively.

In the above-mentioned configuration, every time the timer 33 has counted a predetermined time, the CPU 30 alternately reverses ON/OFF of the control inputs PC1 and PC2 of the ion generator drive circuits 38 via the output interfaces 34. With this, the ion generator drive circuits 38 alternately connect/disconnect between the ground input G1 of the first ion generator 17 or the ground input G2 of the second ion generator 18 and the cathode of the DC power supply E1.

The first ion generator 17 and the second ion generator 18 are driven in one of an alternate drive mode and a full drive mode in a selective manner. In the alternate drive mode, the first ion generator 17 and the second ion generator 18 are alternately driven in a predetermined cycle, whereas in the full drive mode, the first ion generator 17 and the second ion generator 18 are continuously driven at the same time.

Figure 7:
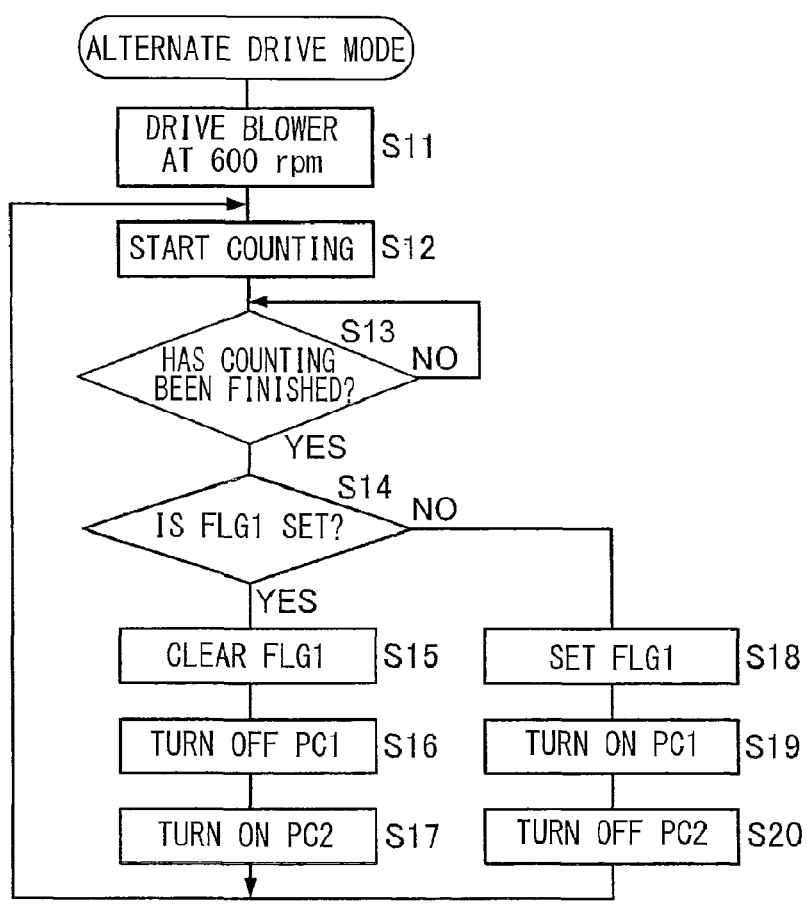
[FIG. 7] A flow chart illustrating an example of processing steps of operation of the ion diffusing apparatus in an alternate drive mode according to the first embodiment of the present invention.

FIG. 7 is a flow chart illustrating an example of processing steps of operation of the ion diffusing apparatus 1 in the alternate drive mode. The alternate drive mode is selected by the operation unit 35, and the ion diffusing apparatus starts to operate. Then, the CPU 30 uses the blower drive control circuit 37 to control the motor 5*m*, thereby rotationally driving the blower 5 at 600 rpm (Step S11). After that, the timer 33 is caused to start counting of one second (Step S12). Then, the CPU 30 determines whether or not the timer 33 has finished the counting (Step S13). When it is determined that the counting has not been finished yet (Step S13: NO), the CPU 30 waits for the timer 33 to finish the counting. When it is determined that the counting has been finished (Step S13: YES), the CPU 30 determines whether or not FLG1 is set (Step S14).

When it is determined that FLG1 is set (Step S14:YES), the CPU 30 clears FLG1 (Step S15). After that, the CPU 30 turns OFF the output of one of the output interfaces 34, to thereby turn OFF the control input PC1 of the ion generation drive circuit 38 (Step S16), whereas the CPU 30 turns ON the output of the other output interface 34, to thereby turn ON the control input PC2 of the ion generator drive circuit 38 (Step S17). Then, the processing returns to Step S12.

When it is determined in Step S14 that FLG1 is not set (Step S14: NO), the CPU 30 sets FLG1 (Step S18). After that, the CPU 30 turns ON the output of the one of the output interfaces 34, to thereby turn ON the control input PC1 of the ion generation drive circuit 38 (Step S19), whereas the CPU 30 turns OFF the output of the other output interface 34 to turn OFF the control input PC2 of the ion generator drive circuit 38 (Step S20). Then, the processing returns to Step S12.

Figure 8:
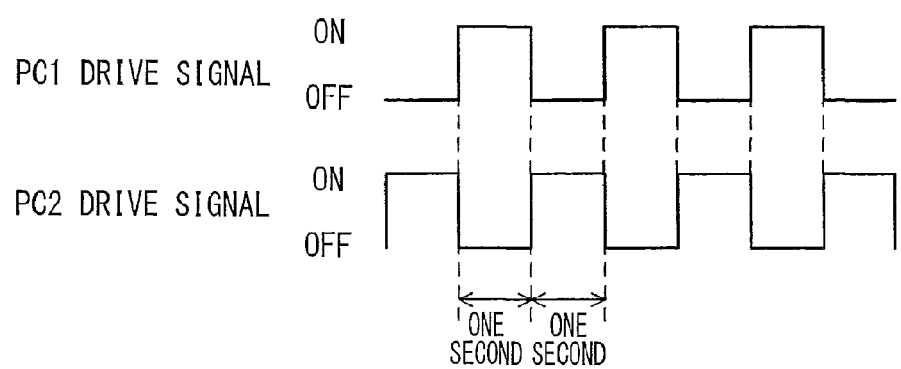
[FIG. 8] A timing chart of drive signals that are input to control inputs PC1 and PC2 from respective output interfaces in the alternate drive mode of the ion diffusing apparatus according to the first embodiment of the present invention.

FIG. 8 is a timing chart of drive signals that are input to the control inputs PC1 and PC2 from the respective output interfaces 34 in the alternate drive mode. Each of the drive signals alternately repeats a one-second ON and a one-second OFF with a duty of 50%. With this, each of the ion generator drive circuits 38 alternately connect/disconnect the power supply to/from the first ion generator 17 and the second ion generator 18 every one second. Accordingly, the first ion generator 17 and the second ion generator 18 are alternately driven in a one-second cycle.

Figure 9A:
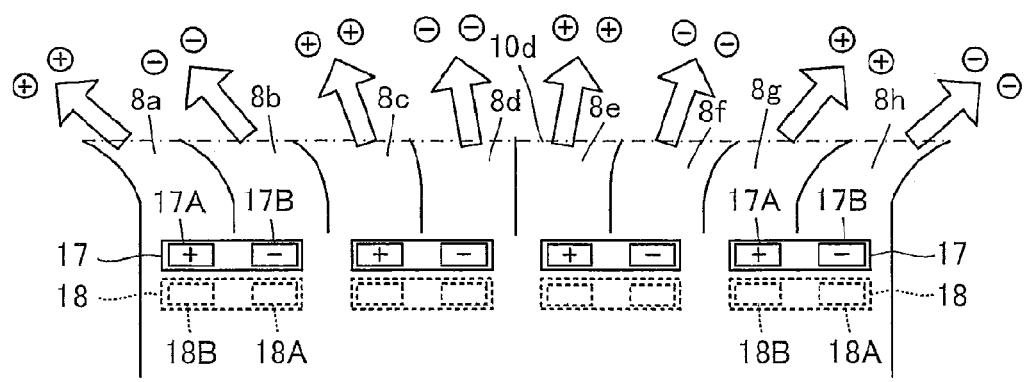
[FIG. 9] Explanatory diagrams illustrating how positive ions and negative ions flowing through laterally-separated paths are delivered to a room in the alternate drive mode of the ion diffusing apparatus according to the first embodiment of the present invention.
Figure 9B:
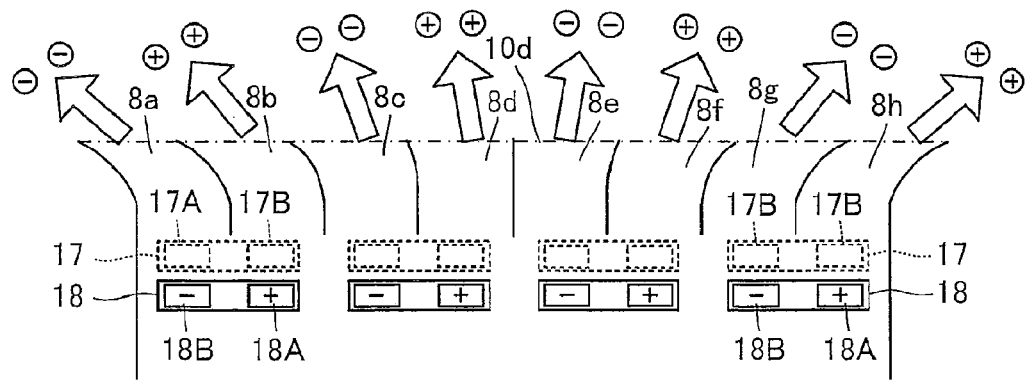

FIG. 9 are explanatory diagrams illustrating how positive ions and negative ions flowing through the laterally-separated paths 8*a* to 8*h* are delivered to the room in the alternate drive mode. In the alternate drive mode, the first ion generator 17 and the second ion generator 18 are alternately driven, thereby forming two alternately-switching areas in the flow direction, that is, an area F1 in which only positive ions flow (see FIG. 3(*a*)) and an area F2 in which only negative ions flow (see FIG. 3(*a*)). In order that states of FIG. 9(*a*) and FIG. 9(*b*) switch alternately, positive ions and negative ions flow through the adjacent laterally-separated paths in an alternately-switching mariner, and are blown out from the opening portion 10*d* of the blowout opening 10. Owing to this, an uneven distribution of positive ions and negative ions in the room can be prevented by avoiding only positive ions flowing through a particular laterally-separated path or only negative ions flowing through a particular laterally-separated path. Therefore, it is possible to diffuse positive ions and negative ions in the room efficiently and evenly.

Figure 10:
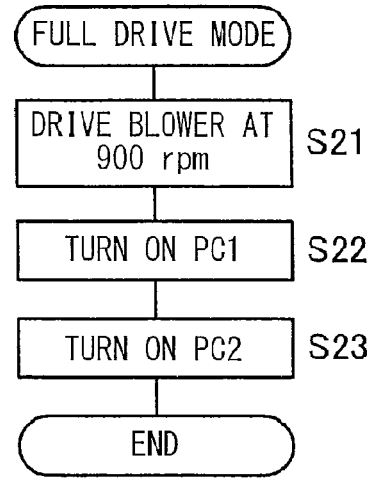
[FIG. 10] A flow chart illustrating an example of processing steps of operation of the ion diffusing apparatus in a full drive mode according to the first embodiment of the present invention.

FIG. 10 is a flow chart illustrating an example of processing steps of operation of the ion diffusing apparatus 1 in the full drive mode. The full drive mode is selected by the operation unit 35, and the ion diffusing apparatus starts to operate. Then, the CPU 30 uses the blower drive control circuit 37 to control the motor 5*m*, thereby rotationally driving the blower 5 at 900 rpm (Step S21). After that, the CPU 30 turns ON the output of the one of the output interfaces 34, to thereby turn ON the control input PC1 of the ion generation drive circuit 38 (Step S22), whereas the CPU 30 turns ON the output of the other output interface 34, to thereby turn ON the control input PC2 of the ion generator drive circuit 38 (Step S23). Then, the processing ends.

Figure 11:
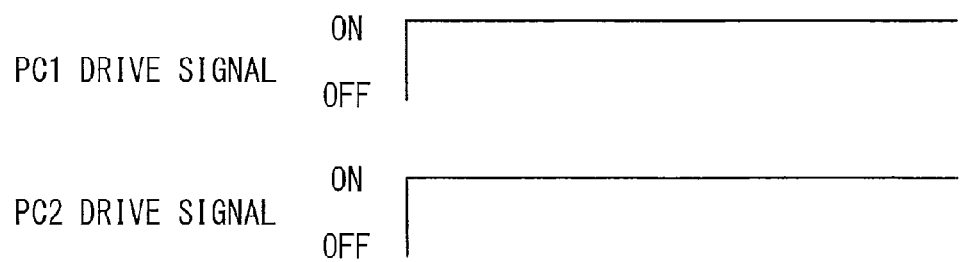
[FIG. 11] A timing chart of drive signals that are input to the control inputs PC1 and PC2 from the respective output interfaces in the full drive mode of the ion diffusing apparatus according to the first embodiment of the present invention.

FIG. 11 is a timing chart of drive signals that are input to the control inputs PC1 and PC2 from the respective output interfaces 34 in the full drive mode. Each of the drive signals is continuously set to be ON. With this, the ion generator drive circuits 38 continuously connect the power supply to the first ion generator 17 and the second ion generator 18, respectively. Thus, the first ion generator 17 and the second ion generator 18 are continuously driven at the same time.

Figure 12:
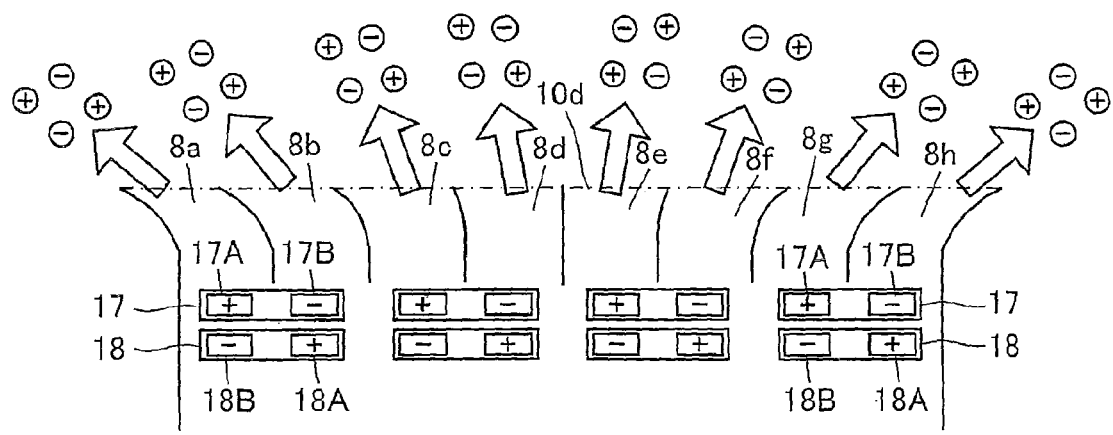
[FIG. 12] An explanatory diagram illustrating how positive ions and negative ions flowing through the laterally-separated paths are delivered to the room in the full drive mode of the ion diffusing apparatus according to the first embodiment of the present invention.

FIG. 12 is an explanatory diagram illustrating how positive ions and negative ions flowing through the laterally-separated paths 8*a* to 8*h* are delivered to the room in the full drive mode. In the full drive mode, the first ion generator 17 and the second ion generator 18 are continuously driven at the same time, thereby simultaneously forming, in the flow direction, two areas in which positive ions and negative ions flow in a coexisting manner, that is, areas F1 and F2 (see FIG. 3(*a*)). As illustrated in FIG. 3(*a*), positive ions and negative ions flow through both the adjacent laterally-separated paths in a coexisting manner, and are then blown out from the opening portion 10*d* of the blowout opening 10. Therefore, positive ions and negative ions delivered from the blowout opening 10 to the room do not have an uneven distribution, and positive ions and negative ions can be diffused in the room in large quantity efficiently and evenly.

Figure 13:
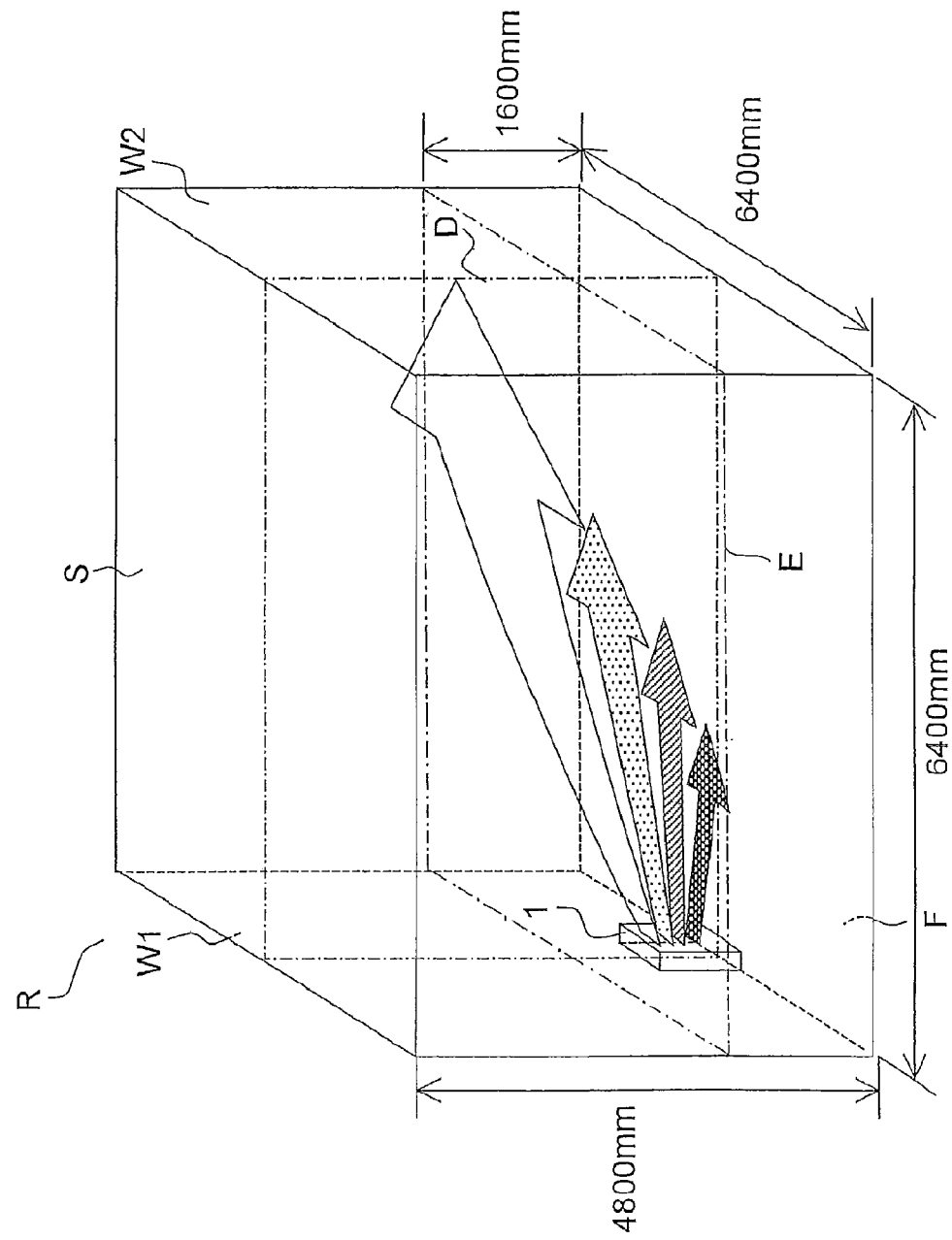
[FIG. 13] A perspective view illustrating a wind blowing state in the room of the ion diffusing apparatus according to the first embodiment of the present invention.
Figure 14:
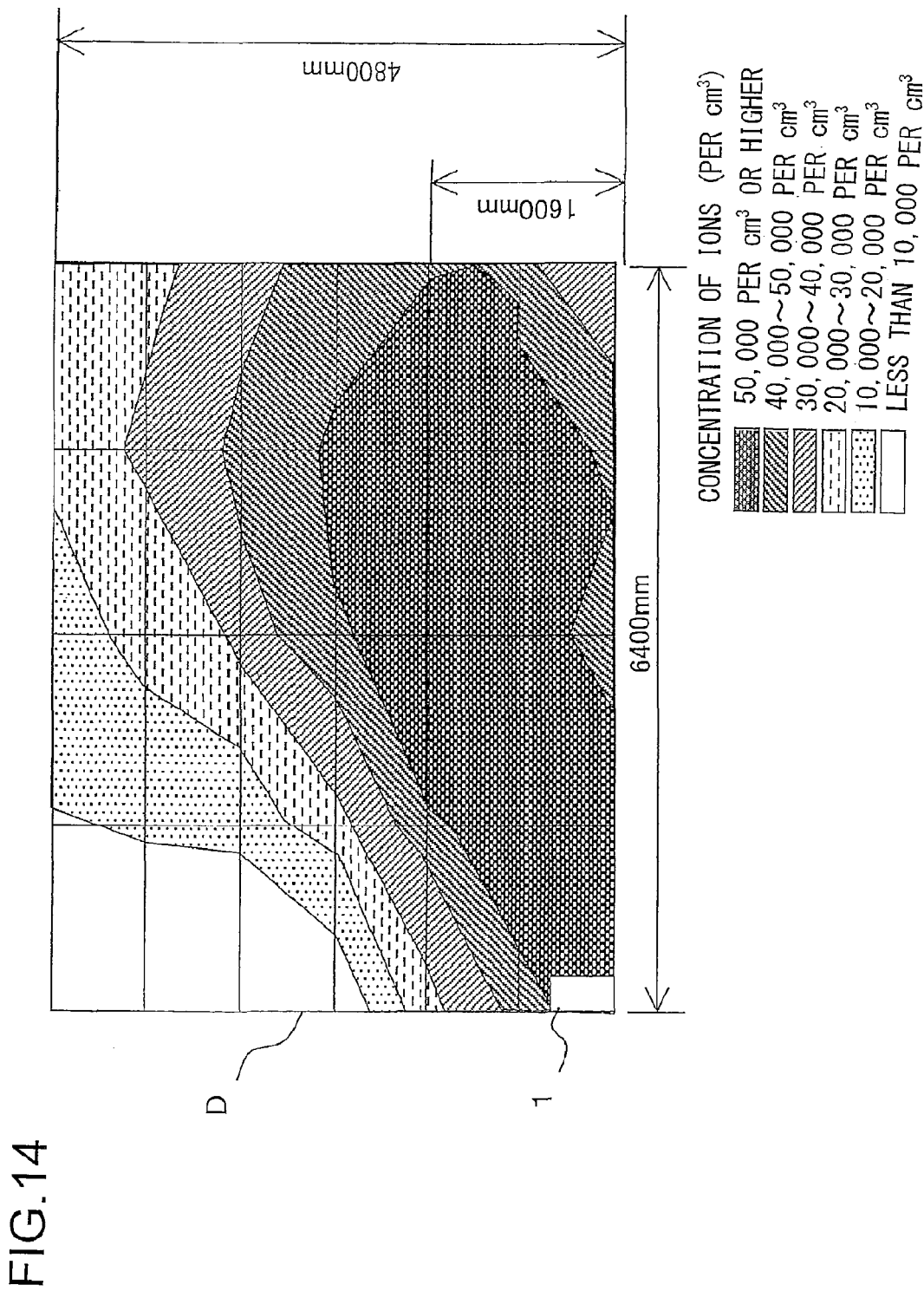
[FIG. 14] A diagram showing results of measuring, with regard to a vertical plane D of FIG. 13, a concentration of ions from the ion diffusing apparatus according to the first embodiment of the present invention.
Figure 15:
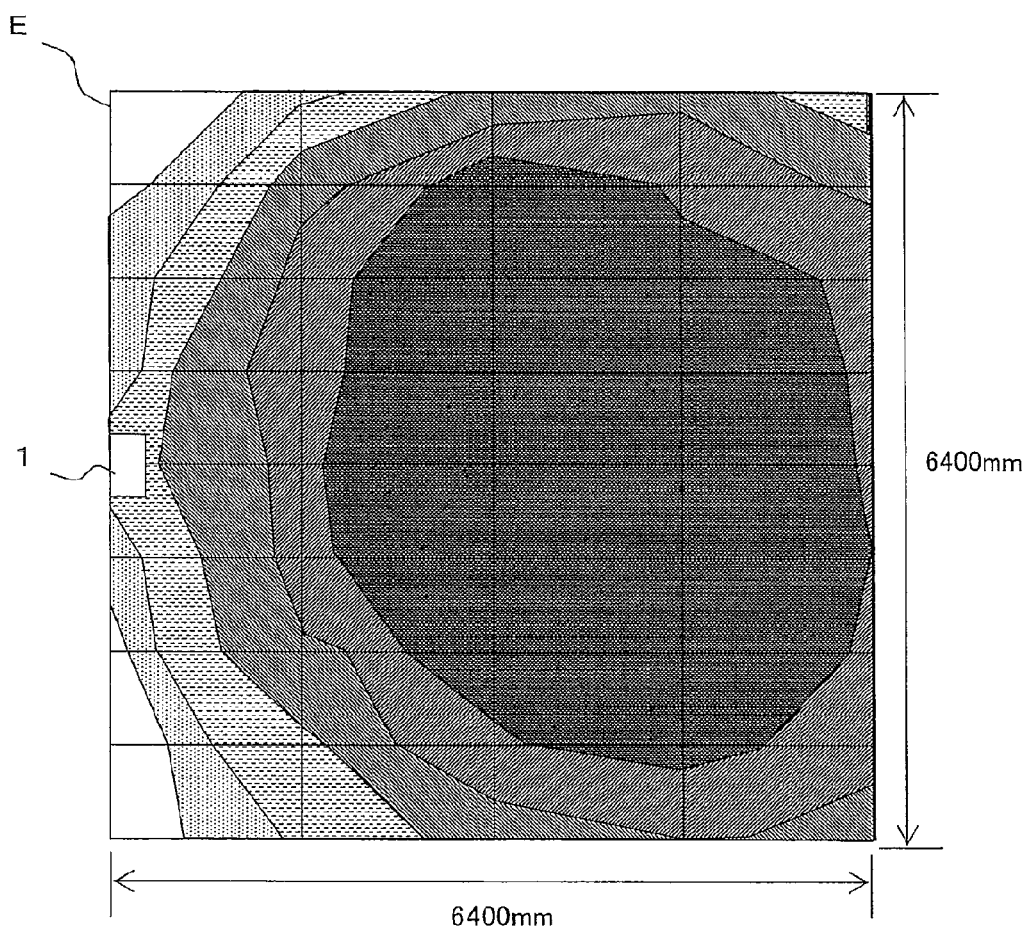
[FIG. 15] A diagram showing results of measuring, with regard to a horizontal plane E of FIG. 13, the concentration of ions from the ion diffusing apparatus according to the first embodiment of the present invention.

FIG. 13, FIG. 14, and FIG. 15 are diagrams for showing results of examining the distribution of the amount of ions in the room when the ion diffusing apparatus 1 according to this embodiment is operated in the alternate drive mode. A room R has a height of 4,800 mm, a width of 6,400 mm, and a depth of 6,400 mm. The area of the room R corresponds to approximately twenty-five tatami mats in terms of the basic standard size of one mat (910 mm×1,820 mm), which is called "saburokuma". The ion diffusing apparatus 1 is placed on a floor surface F adjacent to a side wall W1 on one side, and delivers air currents obliquely upward toward a side wall W2 that faces the side wall W1. Measurement of the amount of ions is performed with regard to a vertical plane D, which passes through the center of the lateral direction of the ion diffusing apparatus 1 and a horizontal plane E, which is positioned at a height of 1,600 mm. Further, a measurement time period is 20 minutes after start of the blowout, and the amount of ions is represented by the concentration of positive ions (per $cm^3$) and the concentration of negative ions (per $cm^3$) in the air.

As illustrated in FIG. 14 and FIG. 15, in this embodiment, upward diffusion of ions and ion loss caused by neutralization of positive ions and negative ions are suppressed, thereby enabling positive ions and negative ions to be widely distributed in the room having the size of several dozen tatami mats, with the amount of ions equal to or higher than 10,000 per $cm^3$. Further, a sufficient concentration of ions is secured for such an area that can be always used as a living space in the room, that is, a living area excluding the four corners of the room and an upper space positioned higher than 2 m. Thus, by disposing a plurality of the ion diffusing apparatuses according to this embodiment with given spacings, it is possible to secure a sufficient concentration of ions for areas where people spend time, such as a hotel, a lobby of an airport or the like, and a waiting room of a hospital. Owing to this, it is possible to enhance a sterilization effect on airborne bacteria in the room, an inactivation effect on viruses, and an effect of removing odors absorbed in a curtain, clothing, etc.

<Second Embodiment>

Figure 16:
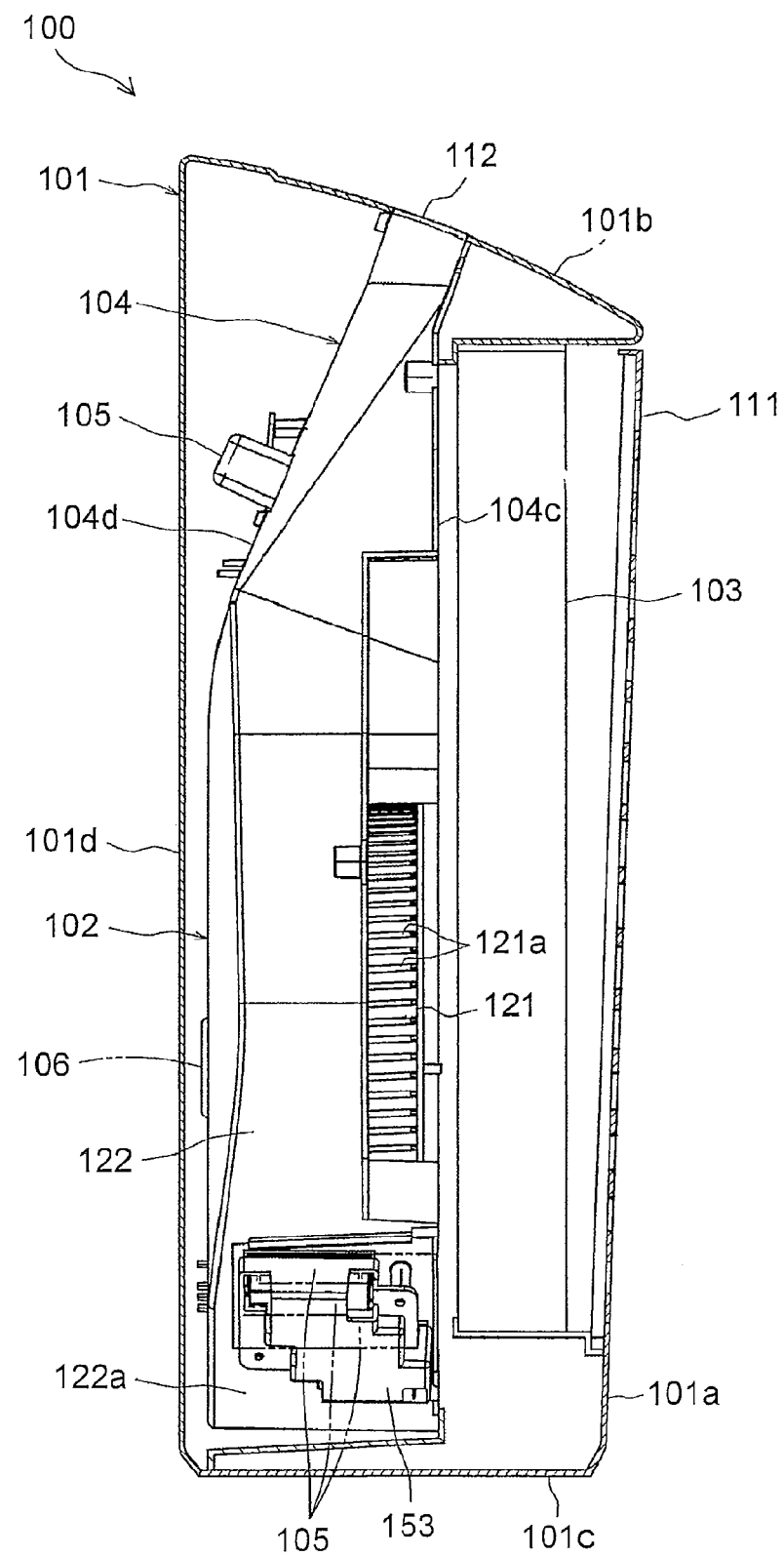
[FIG. 16] A longitudinal side sectional view illustrating structure of an air purifying apparatus according to a second embodiment of the present invention.
Figure 17:
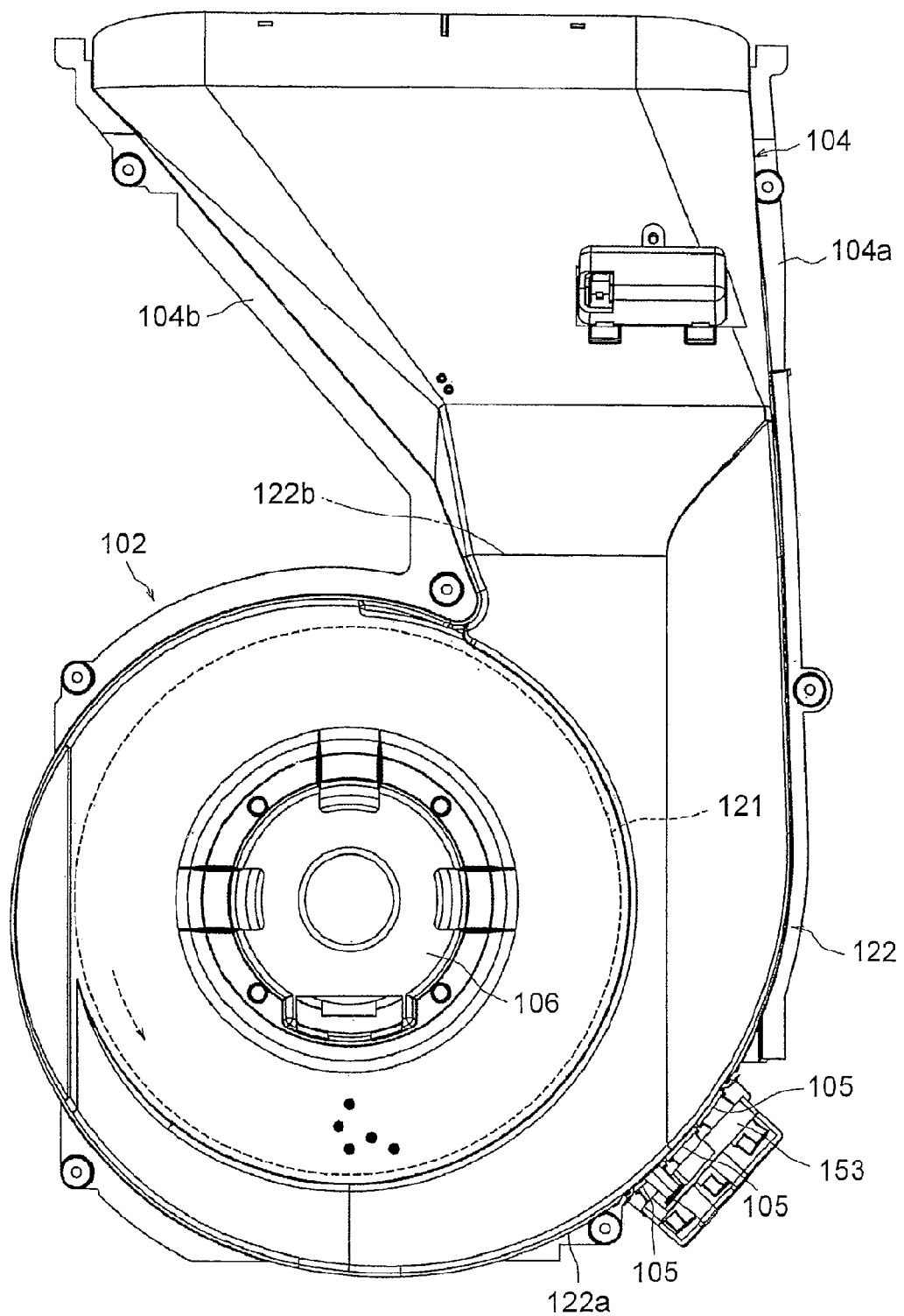
[FIG. 17] A front view illustrating structure of a main part of the air purifying apparatus according to the second embodiment of the present invention.
Figure 18:
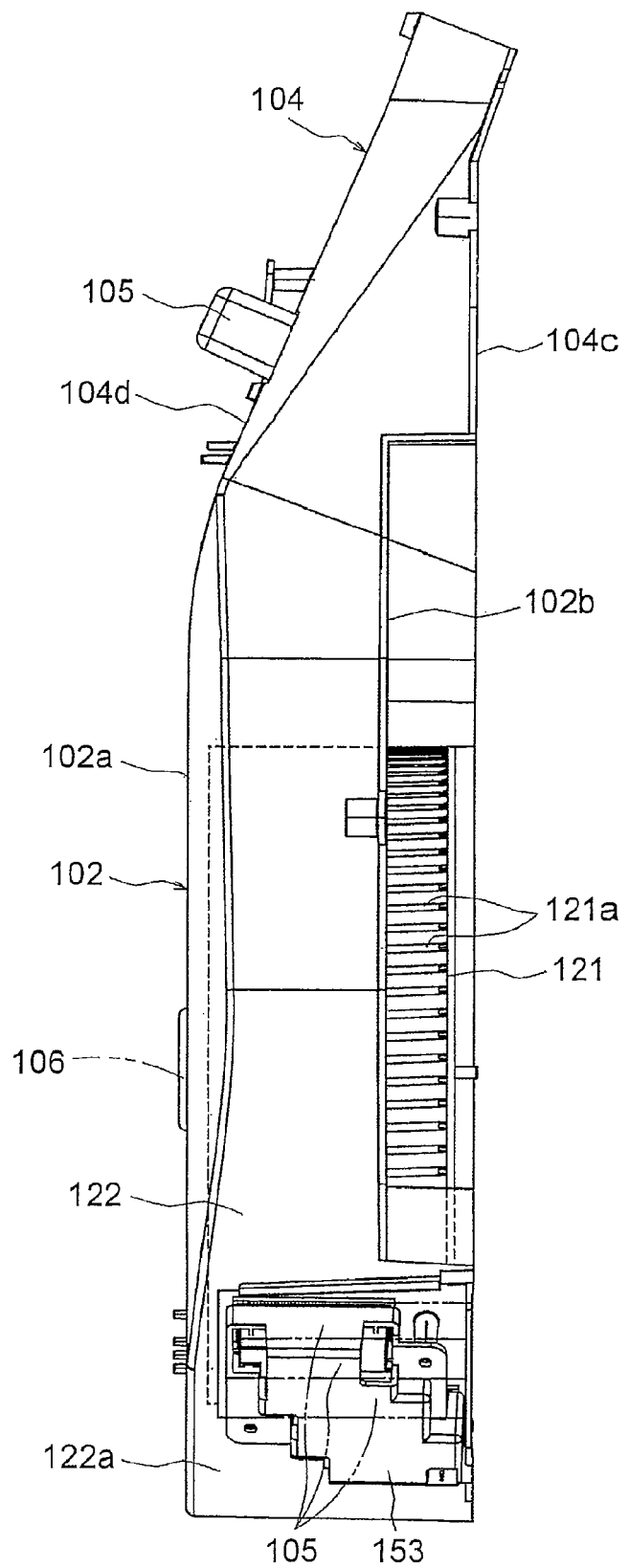
[FIG. 18] A side view illustrating structure of a main part of the air purifying apparatus according to the second embodiment of the present invention.
Figure 19A:
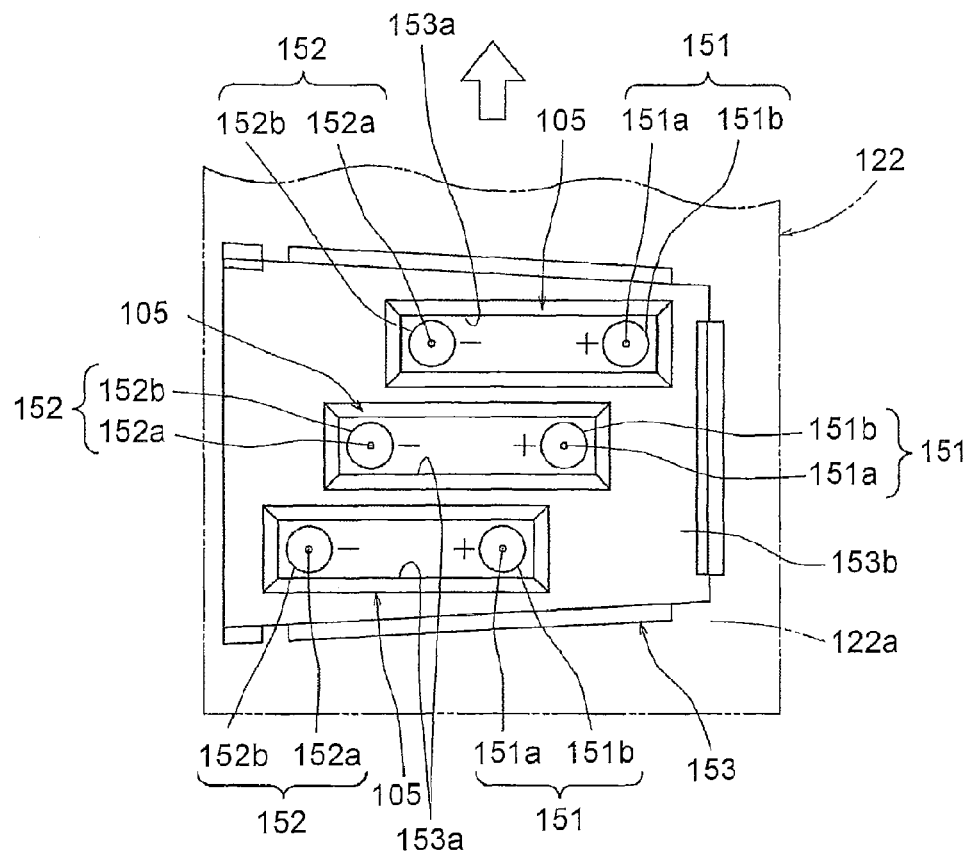
[FIG. 19] A front view (FIG. 19(a)) and a side view (FIG. 19(b)) illustrating structure of ion generators of the air purifying apparatus according to the second embodiment of the present invention.
Figure 19B:
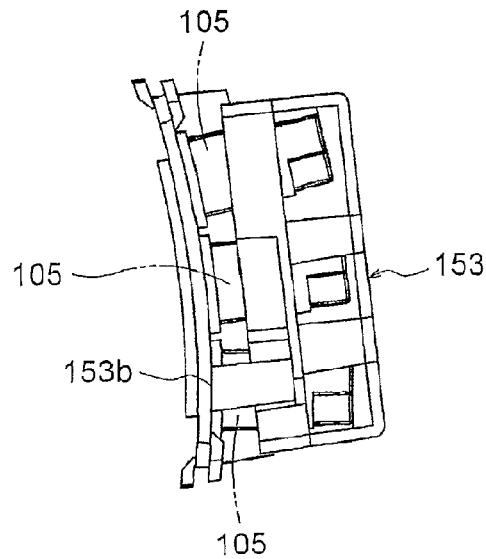

FIG. 16 is a longitudinal side sectional view illustrating structure of an air purifying apparatus according to a second embodiment of the present invention. FIG. 17 is a front view illustrating structure of a main part. FIG. 18 is a side view illustrating structure of a main part. FIG. 19 illustrate structure of an ion generator, with FIG. 19(a) being a front view and FIG. 19(b) being a side view.

An air purifying apparatus 100 illustrated in FIG. 16 includes: a housing 101 having a suction opening 111 in a back wall 101a and a blowout opening 112 in a top wall 101b; a blower 102 disposed in a lower portion of the housing 101; a filter 103 that is disposed on an inner side of the suction opening 111, and, by allowing air sucked in from the suction opening 111 by the blower 102 to pass therethrough, removes contaminants in the air to clean the air; a duct 104 that is disposed between the blower 102 and the blowout opening 112, and serves as a flow path for allowing the air to flow through to the blowout opening 112; and an ion generator 105 that includes two ion generation portions 151 and 152, and adds positive ions and negative ions to the air blown from the blower 102, and the air purifying apparatus 100 is configured so that positive ions and negative ions generated by the ion generation portions 151 and 152 are added to the air blown from the blower 102, and the positive ions and the negative ions are emitted along with the air to the outside from the blowout opening 112.

The housing 101 has a substantially rectangular parallelopiped shape including a bottom wall 101c being rectangular in plan view, a front wall 101d and the back wall 101a extending from two sides of the bottom wall 101c, side walls extending from the other two sides of the bottom wall 101c, and the top wall 101b. The back wall 101a is provided with the suction opening 111 having a rectangular shape with a longitudinal direction thereof corresponding to the vertical direction, and the top wall 101b is provided with the blowout opening 112 having a rectangular shape with a longitudinal direction thereof corresponding to both side wall sides.

The blower 102 has a cylindrical shape and is of a centrifugal type including an impeller 121 disposed such that a rotational axis thereof corresponds to an anteroposterior direction and a casing 122 accommodating the impeller 121 in a rotatable manner. A motor 106 for driving the impeller 121 is mounted on a front side portion of the casing 122.

The impeller 121 is a multi-blade fan including a plurality of blades 121a each having a rotation center side thereof displaced, with respect to an outer edge thereof, toward a rotational direction. In other words, the impeller 121 is a cylindrically-shaped sirocco fan, which has one end thereof provided with a bearing plate, where an output shaft of the motor 106 is inserted to a shaft hole provided at the center, and discharges air, which is sucked into a hollow in a center portion of the fan from an opening provided to the other end of the fan, from between the blades 121a provided to a circumferential portion of the fan.

The casing 122 includes a circular guide wall 122a, which guides air currents generated by the rotation of the impeller 121 toward the rotational direction of the impeller 121 to generate a laminar flow, thereby increasing the speed of the air currents, and an air outlet 122b, which is open upward in one tangential direction of the circular guide wall 122a from part of the circular guide wall 122a. The air outlet 122b has a squared-cylindrical shape that protrudes in the one tangential direction of the circular guide wall 122a from the part of the circular guide wall 122a. Further, the casing 122 includes a casing main body 102a, which has a dish shape and includes the circular guide wall 122a and an open portion for the air outlet 122b, and a cover plate 102b, which is open in a portion corresponding to the opening of the impeller 121 and covers an open side of the casing main body 102a. The cover plate 102b is mounted to the casing main body 102a with a plurality of male screws.

The circular guide wall 122a of the casing 122 structured as described above is provided with through holes corresponding to the ion generation portions 151 and 152 and a mounting hole spaced apart from the through holes. The ion generator 105 is mounted with a male screw being screwed into the mounting hole.

The duct 104 has a squared-cylindrical shape, which has a lower end thereof connected to the air outlet 122b and an upper end thereof being open, and is integrally formed with the casing main body 102a and the cover plate 102b. Further, the duct 104 includes: one side wall 104a disposed along the one tangential direction of the circular guide wall 122a from the air outlet 122b; another side wall 104b whose distance from the one side wall gradually becomes longer with the distance at the air outlet 122b being the shortest; a back wall 104c disposed vertically; and a front wall 104d whose distance from the back wall 104c gradually becomes shorter with the distance at the air outlet 122b being the longest. The back wall 104c and the front wall 104d extend from the one side wall 104a and the another side wall 104b. The duct 104 guides air blown out from the air outlet 122b along the one side wall 104a, the back wall 104c, and the front wall 104d, to thereby generate a laminar flow. Further, the front wall 104d is provided with the through holes corresponding to the ion generation portions 151 and 152 and the mounting hole spaced apart from the through holes. The ion generator 105 is mounted with the male screw being screwed into the mounting hole.

As illustrated in FIG. 19, the ion generator 105 includes: the pair of ion generation portions 151 and 152 spaced apart from each other in the direction intersecting the flow direction of the air delivered from the blower 102; a power feeding portion for applying voltage to the ion generation portions 151 and 152; and a holding member 153 for holding the ion generation portions 151 and 152 and the power feeding portion. When the power feeding portion applies voltage to the ion generation portions 151 and 152, the ion generation portions 151 and 152 perform corona discharge, to thereby generate ions. The principle of generation of positive ions and negative ions is as described above.

The ion generation portions 151 and 152 include discharge electrode projecting portions 151a and 152a having a sharp pointed shape, and induction electrode rings 151b and 152b respectively surrounding the discharge electrode projecting portions 151a and 152a, and the discharge electrode projecting portions 151a and 152a are disposed in center portions of the induction electrode rings 151b and 152b, respectively. The ion generation portion 151 generates positive ions, whereas the ion generation portion 152 generates negative ions. The principle of generation of positive ions and negative ions is as described above.

The ion generator 105 is mounted on the circular guide wall 122a of the casing 122 and the front wall 104d of the duct 104, and the pair of ion generation portions 151 and 152 are disposed at positions intersecting the flow direction in which air flows.

Three ion generators 105 mounted on the circular guide wall 122a of the casing 122 are held by a single holding member 153. The three ion generators 105 are disposed in parallel while being spaced apart from one another in the flow direction (circular direction of the circular guide wall 122a), and are also relatively displaced in the direction intersecting the flow direction (rotational axis direction of the impeller 121). Further, the ion generation portions 151 and 152 of the three ion generators 105 have the same polarities in the direction in which the ion generation portions 151 and 152 are relatively displaced, and are also disposed so as not to overlap one another in the flow direction. Each of the ion generation portions 151 and 152 of the ion generators 105 faces an inside of the casing 122 via the through hole. Further, a side of the holding member 153, which is mounted on the casing 122, includes a curved surface 153b that is curved in the flow direction and has three openings 153a corresponding to the respective ion generation portions 151 and 152. The ion generation portions 151 and 152 are disposed in each of the openings 153a of the curved surface 153b.

The air purifying apparatus 100 structured as described above is placed near a wall of a room with the suction opening 111 positioned on the wall side.

When the blower 102 is driven, the impeller 121 is rotated, thereby sucking in air in the room from the suction opening 111 into the housing 101. An air flow path is generated between the suction opening 111 and the blowout opening 112, and sucked-in contaminants in the air, such as dust particles, are removed by the filter 103 to generate cleaned air.

The air passing through the filter 103 is sucked into the casing 122 of the blower 102. On this occasion, the air sucked into the casing 122 is caused to form a laminar flow by the circular guide wall 122a provided around the impeller 121. The air flowing in the form of the laminar flow is guided along the circular guide wall 122a to the air outlet 122b, and is then blown out from the air outlet 122b into the duct 104.

The ion generation portions 151 and 152 are disposed on the circular guide wall 122a of the casing 122 of the blower 102, and hence it is possible to efficiently add ions generated from the ion generation portions 151 and 152 to the air flowing in the form of the laminar flow through a relatively narrow path along the circular guide wall 122a. Further, the air flowing along the circular guide wall 122a has high wind speed, and hence it is possible to add ions to the air further efficiently.

Further, the ion generator 105 has the pair of ion generation portions 151 and 152 at positions intersecting the flow direction of the air, and thus has more positions for adding ions for the first time to the air. As a result, it is possible to add ions to the air further efficiently.

Further, three ion generators 105 are disposed so as to be spaced apart from one another in the flow direction of the cleaned air, and are relatively displaced in the direction intersecting the flow direction so that the ion generation portions 151 and 152 of the ion generators 105 do not overlap one another in the flow direction, thereby providing more positions for adding ions for the first time to the air. This prevents positive ions and negative ions generated from the ion generation portions 151 and 152 of the respective ion generators 105 from being neutralized, and hence it is possible to add ions to the air further efficiently without making the size of the casing 122 larger.

The positive ions and negative ions added to the air flowing in the form of the laminar flow as described above become mixed when the air is blown out from the air outlet 122b of the casing 122 into the duct 104.

The duct 104 is structured to cause the air to flow in the form of the laminar flow along the one side wall 104a, the back wall 104c, and the front wall 104d, and the ion generation portions 151 and 152 are disposed on the front wall 104d for causing the air to flow in the form of the laminar flow. Therefore, it is possible to further add positive ions and negative ions generated from the ion generation portions 151 and 152 disposed in the duct 104 to the air to which positive ions and negative ions have been added in the casing 122 of the blower 102, resulting in an increased amount of ions in the air.

Figure 20:
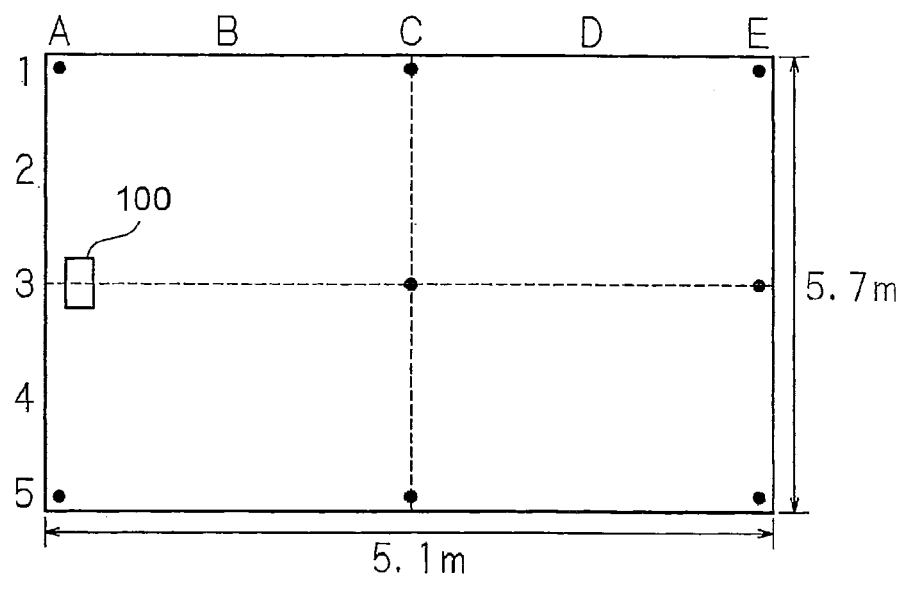
[FIG. 20] A sketch used for measurement performed in a room on air blown out from a blowout opening of the air purifying apparatus according to the second embodiment of the present invention which is placed on a floor of the room.

FIG. 20 is a sketch used for measurement performed in a room on air blown out from the blowout opening of the air purifying apparatus according to the present invention which is placed on a floor of the room. FIG. 21 shows data indicating results of measurement on the amount of ions in the room. The results shown in FIG. 21 were obtained when the amount of ions was measured at points A to E in the room with regard to a conventional air purifying apparatus including an ion generator and the air purifying apparatus according to the present invention. Referring to FIG. 20, the room has a floor area of 5.1 m×5.7 m (approximately eighteen tatami mats in terms of the size of one "saburokuma" tatami mat), and the air purifying apparatus is placed on the floor, being spaced apart by 0.3 m from one wall on a 5.7-m side. Further, measurement points A represent such positions that correspond to points 1, 3, and 5 of the 5.7-m side and are spaced apart by 0.1 m from one wall on a 5.1-m side of the room. Measurement points C represent such positions that correspond to the points 1, 3, and 5 of the 5.7-m side and are at the center along the 5.1-m side of the room. Measurement points E represent such positions that correspond to the points 1, 3, and 5 of the 5.7-m side and are spaced apart by 0.1 m from another wall on the 5.1-m side of the room. Further, the measurement time period is 20 minutes from the start of blowout, and the amounts of ions are expressed by the concentration of positive ions (per $cm^3$) and the concentration of negative ions (per $cm^3$) in the air.

According to the measurement results of FIG. 21, an average amount of ions of the measurement points was 39,611 per cm³ and the rate of increase was 154%. Thus, it has been demonstrated that the amount of ions emitted in the room can be increased. According to this embodiment, it is possible to widely distribute positive ions and negative ions in a room having a size of several tatami mats, with the amount of ions equal to or higher than 10,000 per cm³. Owing to this, it is possible to enhance the sterilization effect on airborne bacteria in the room, the inactivation effect on viruses, and the effect of removing odors absorbed in a curtain, clothing, etc.

Here, in this embodiment, three ion generators 5 are disposed on the circular guide wall 122a of the casing which is structured to cause air to flow in the form of the laminar flow, and one ion generator 105 is disposed on the front wall 104d of the duct 104 which is structured to cause air to flow in the form of the laminar flow. However, apart from that, any structure may be employed as long as the ion generator 105 is disposed in a laminar flow portion structured to cause air to flow in the form of the laminar flow. A position at which the ion generator 105 is disposed is not particularly limited. For example, the ion generator 105 is disposed on at least one of a portion on the boundary between the air outlet 122b and the circular guide wall 122a, the circular guide wall 122a, and the front wall 104d of the duct 104.

<Third Embodiment>

Figure 22:
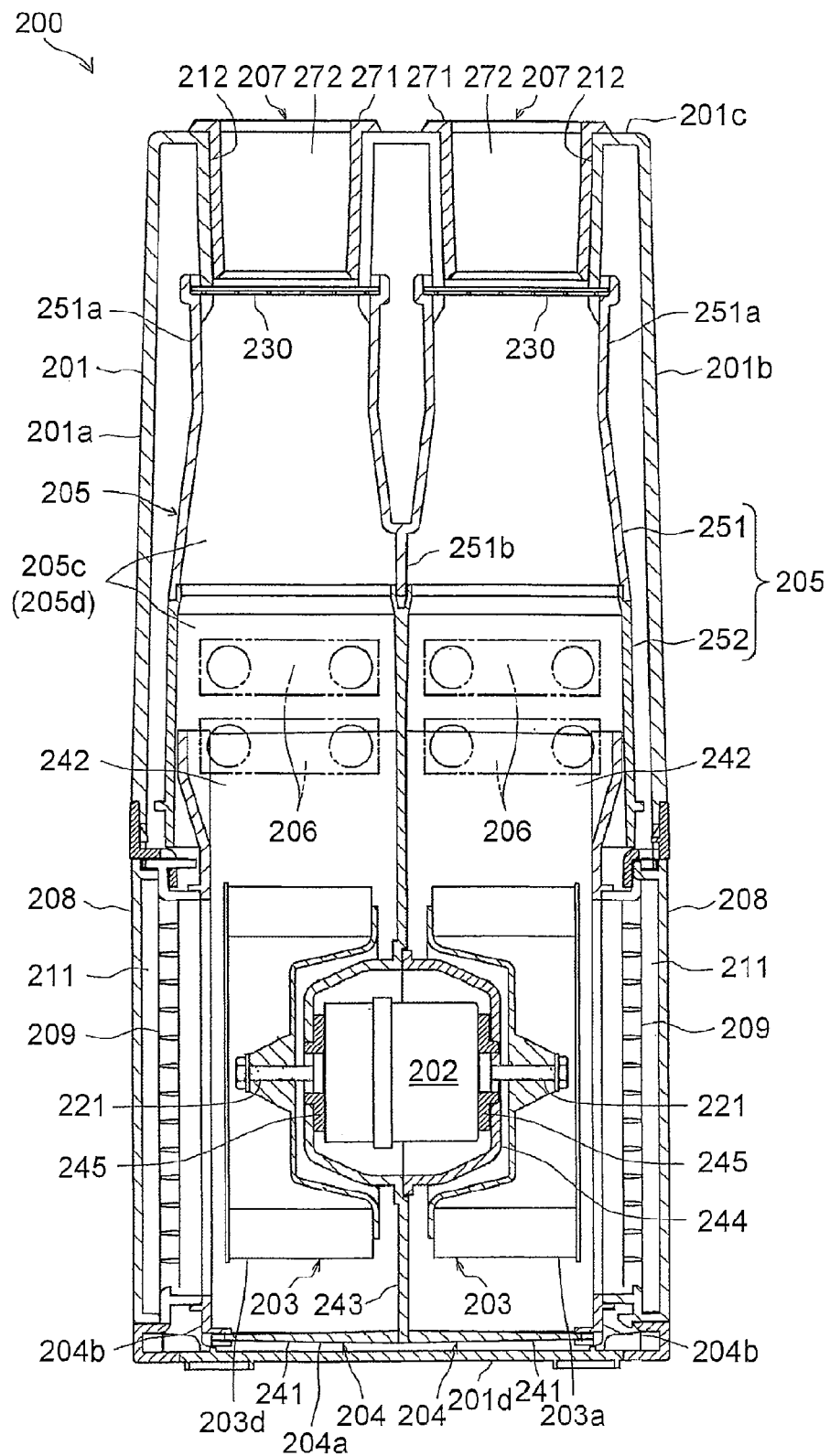
[FIG. 22] A longitudinal front sectional view illustrating structure of an ion emitting apparatus according to a third embodiment of the present invention.
Figure 23:
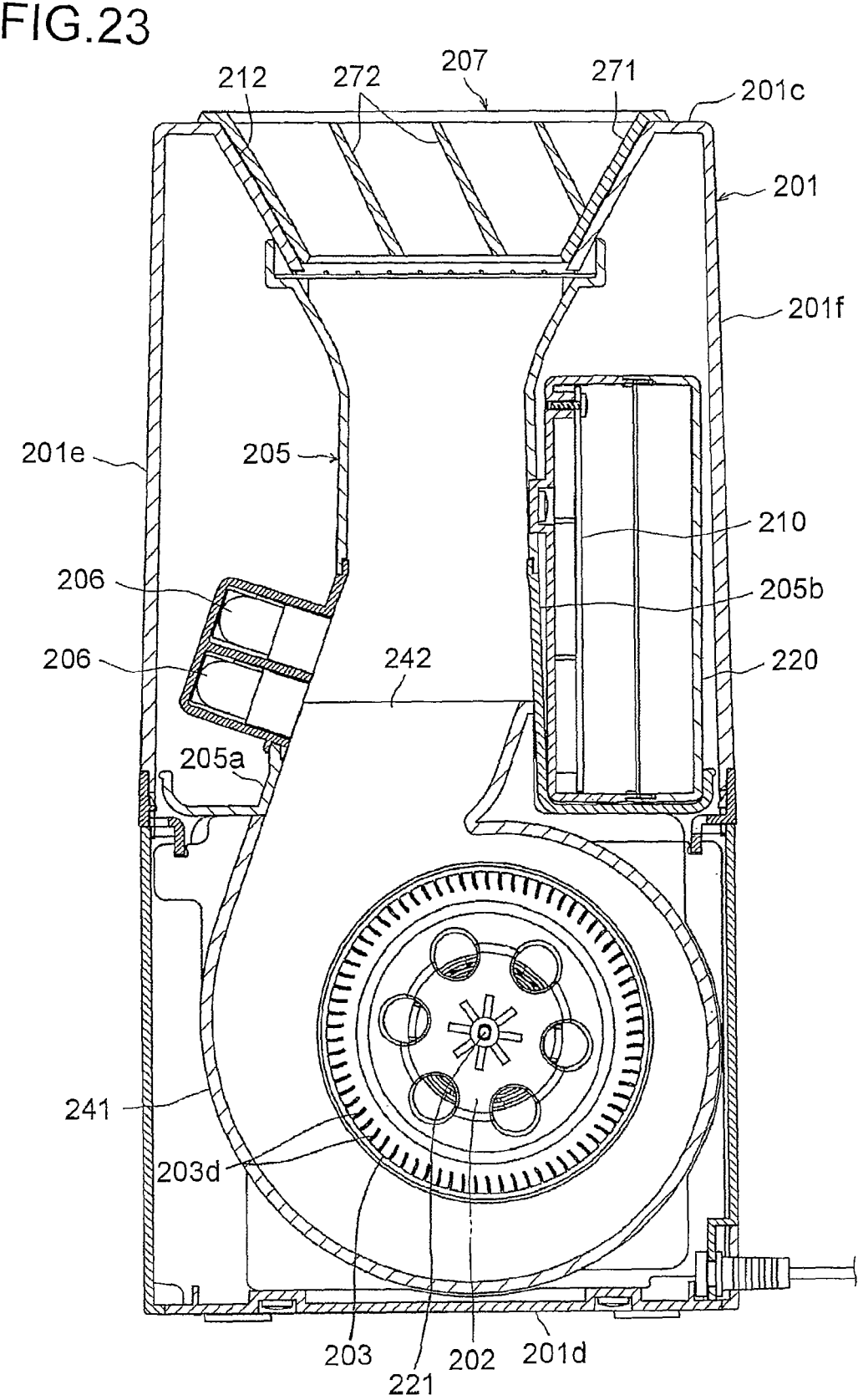
[FIG. 23] A longitudinal side sectional view illustrating the structure of the ion emitting apparatus according to the third embodiment of the present invention.
Figure 24:
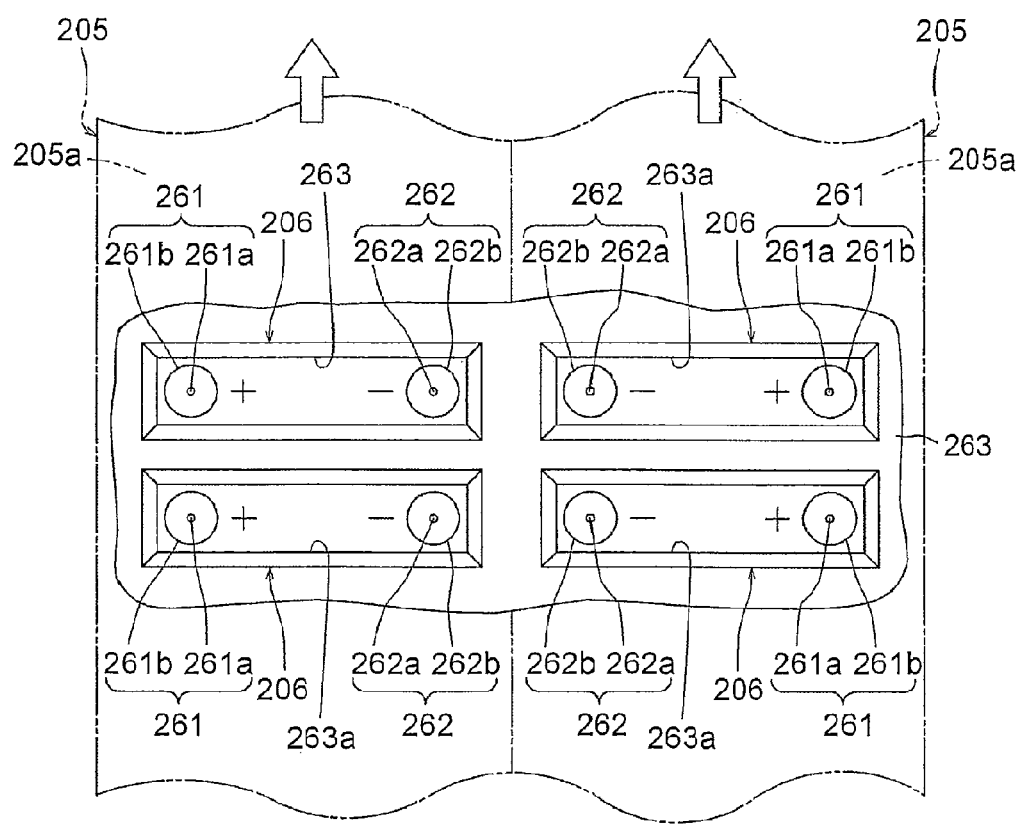
[FIG. 24] A front view illustrating partially-omitted structure of ion generators of the ion emitting apparatus according to the third embodiment of the present invention.

FIG. 22 is a longitudinal front sectional view illustrating structure of an ion emitting apparatus according to a third embodiment of the present invention, FIG. 23 is a longitudinal side sectional view illustrating the structure of the ion emitting apparatus, and FIG. 24 is a front view illustrating partially-omitted structure of ion generators.

An ion emitting apparatus 200 illustrated in FIG. 22 includes: a housing 201 having suction openings 211 in lower portions of both side walls 201a and 201b facing each other with a space therebetween, and having two fitting holes 212 in a center portion of a top wall 201c; a motor 202 that is disposed in a lower portion of the housing 201 and has output shafts 221 on both sides of an output shaft direction; two impellers 203 mounted to the output shafts 221 of the motor 202; two casings 204 respectively accommodating the impellers 203 in a rotatable manner; two ducts 205 being cylindrical portions for causing air currents generated by the rotation of the impellers 203 to flow upward in a separated manner; ion generators 206 each including two ion generation portions 261 and 262 and disposed in the middle of the ducts 205; and wind direction members 207 disposed in the fitting holes 212 in a detachable manner. Note that, the motor 202, the impellers 203, and the casings 204 constitute a blower.

The housing 201 has a substantially rectangular parallelepiped shape including a bottom wall 201d being rectangular in a planar view, a front wall 201e and a back wall 201f extending from two sides of the bottom wall 201d, the side walls 201a and 201b extending from the other two sides of the bottom wall 201d, and the top wall 201c. The suction openings 211 in the lower portions of both the side walls 201a and 201b are provided with filters 208 that, by allowing air sucked in from the suction openings 211 by the impellers 203 to pass through, removes contaminants in the air to clean the air. The fitting holes 212 of the top wall 201c each have a rectangular shape having a longitudinal direction thereof corresponding to the anteroposterior direction, and have an inner surface on the front side inclined forward with respect to the vertical direction and an inner surface on the back side inclined backward with respect to the vertical direction. Further, the housing 201 is divided into an upper division and a lower division in the middle of the vertical direction, and the casings 204 are mounted to the lower division whereas the ducts 205 are mounted to the upper division.

The impellers 203 are each a multi-blade fan including a plurality of blades 203d each having a rotation center side thereof displaced, with respect to an outer edge thereof, toward a rotational direction. In other words, the impellers 203 are each a cylindrically-shaped sirocco fan, which has one end thereof provided with a bearing plate, where the output shaft 211 of the motor 202 is inserted to a shaft hole provided at the center, and discharges air, which is sucked into a hollow in a center portion of the fan from an opening provided to the other end of the fan, from between the blades 203a positioned in a circumferential portion of the fan.

The casings 204 each include a circular guide wall 241, which guides air currents generated by the rotation of the impeller 203 toward the rotational direction of the impeller 203, thereby increasing the speed of the air currents, and an air outlet 242, which is open upward in one tangential direction of the circular guide wall 241 from part of the circular guide wall 241. The air outlets 242 each have a squared-cylindrical shape that protrudes in the one tangential direction of the circular guide wall 241 and in a direction inclined with respect to the vertical direction from the part of the circular guide wall 241. Further, the casings 204 each include a casing main body 204a, which has a dish shape and includes the circular guide wall 241 and an open portion for the air outlet 242, and a cover plate 204b, which is open in a portion corresponding to the opening of the impeller 203 and covers an open side of the casing main body 204a. Facing sides of the respective casing main bodies 204a are integrally joined together with a joint wall 243 for partitioning. Further, a ventilation plate 209 having a plurality of air holes is provided between an open portion of the cover plate 204b and the filter 208.

A portion of the joint wall 243, which corresponds to the motor 202, has a concave portion that is recessed toward one of the casing main bodies 204a, and a supporting plate 244 having a dish shape is mounted to a rim portion of the concave portion. The motor 202 is held in a sandwiched manner between center portions of the concave portion and the supporting plate 244 through an intermediation of rubber plates 245. The output shafts 221 are inserted through shaft holes provided to the center portions of the concave portion and the supporting plate 244, and the impellers 203 are mounted to the output shafts 221. Further, an upper end of the joint wall 243 extends upward beyond the casings 204.

The ducts 205 each have a lower end thereof connected to the air outlet 242 and an upper end thereof connected to the fitting hole 212, and are each formed of a cylindrical portion having a squared-cylindrical shape that has a middle thereof in the vertical direction made narrower. Further, the ducts 205 each include: a front wall 205a disposed along the one tangential direction of the circular guide wall 241 from the air outlet 242; a back wall 205b disposed substantially vertically from the air outlet 242; and two side walls 205c and 205d that extend from the front wall 205a and the back wall 205b and are disposed substantially vertically. Air blown out from the air outlet 242 is caused to form a laminar flow along the front wall 205a and the side walls 205c and 205d, and to flow along the vertical direction.

The front walls 205a are each provided with through holes corresponding to the ion generation portions 261 and 262, and the ion generator 206 is mounted to the through holes through insertion. The back walls 205b are each mounted with a circuit board 210 connected to the motor 202, the ion generator 206, and a power supply line and with a cover 220 covering the circuit board 210. Further, the ducts 205 are divided into a duct upper division 251 and a duct lower division 252 in the middle of the vertical direction. The duct lower division 252 has a squared-cylindrical shape, and the center of a lateral direction thereof is partitioned by the joint wall 243. In the duct upper division 251, lower portions of squared-cylindrical portions 251a disposed in parallel while being spaced apart from each other in the lateral direction are integrally jointed by a joint portion 251b, and are partitioned by the joint portion 251b and the joint wall 243. Further, upper ends of the duct upper division 251 are provided with protection screens 230 for preventing a foreign object, such as a finger, from entering from the outside.

As illustrated in FIG. 24, the ion generators 206 each include: the pair of ion generation portions 261 and 262 spaced apart from each other in the direction intersecting the flow direction of the air generated by the rotation of the impeller 203 (see FIG. 22); a power feeding portion for applying voltage to the ion generation portions 261 and 262; and a holding member 263 for holding the ion generation portions 261 and 262 and the power feeding portion. When the power feeding portion applies voltage to the ion generation portions 261 and 262, the ion generation portions 261 and 262 perform plasma discharge, to thereby generate ions.

The ion generation portions 261 and 262 include discharge electrode projecting portions 261a and 262a having a sharp pointed shape, and induction electrode rings 261b and 262b respectively surrounding the discharge electrode projecting portions 261a and 262a, and the discharge electrode projecting portions 261a and 262a are disposed in center portions of the induction electrode rings 261b and 262b, respectively. The ion generation portion 261 generates positive ions, whereas the ion generation portion 262 generates negative ions. The principle of generation of positive ions and negative ions is as described above.

Two ion generators 206 are held by a single holding member 263. The pair of ion generators 206 are mounted on each of the front walls 205a of the ducts 205, and are disposed in parallel while being spaced apart from each other in the flow direction. Further, the ion generation portions 261 and 262 of each of the pair of ion generators 206 are disposed side by side at positions intersecting the flow direction, and the polarities of the ion generation portions on adjacent sides are made identical. The ion generation portions 261 and 262 of each of the ion generators 206 face an inside of each of the ducts 205 via the through holes. Further, a side of the holding member 263, which is mounted onto the ducts 205, has four openings 263a corresponding to the respective ion generation portions 261 and 262, and the ion generation portions 261 and 262 are disposed in the respective openings 263a.

As illustrated in FIG. 23, the wind direction members 207 each include a cornered frame portion 271 whose cross section in the anteroposterior direction has an inverted trapezoid shape, and a plurality of wind direction plates 272 that are disposed in parallel in the cornered frame portion 271 while being spaced apart from each other in the anteroposterior direction and are inclined one side of the anteroposterior direction with respect to the vertical direction. The wind direction members 207 are formed to have an identical shape. Front and back walls of each of the cornered frame portions 271 are inclined forward and backward, respectively.

The ion emitting apparatus 200 structured as described above is placed in a room. When the motor 202 of the blower is driven, the impellers 203 are rotated, thereby sucking in air in the room from the suction openings 211 on both sides into the casings 4. Sucked-in contaminants in the air, such as dust particles, are removed by the filters 208. On this occasion, the air sucked into the casings 204 is caused to form laminar flows by the circular guide walls 242 provided around the impellers 203. The air in the form of the laminar flow flows along the circular guide walls 241 to the air outlets 242, and is then blown out from the air outlets 242 into the ducts 205.

The ducts 205 are structured to cause air to flow in the form of the laminar flow along the front walls 205a and the side walls 205c and 205d. The ion generators 206 are disposed on the front walls 205a for causing air to flow in the form of the laminar flow, and hence it is possible to efficiently add positive and negative ions generated from the ion generation portions 261 and 262 of the ion generators 206 to the air flowing in the form of the laminar flow through a relatively narrow path along the front walls 205a. Further, the ducts 205 are structured to be narrow in the middle of the vertical direction so that the air flows with high wind speed, and hence it is possible to efficiently add positive ions and negative ions to the air. Further, a plurality of the ion generators 206 are disposed so as to be spaced apart from each other in the flow direction of the air, thereby providing more positions for adding ions to the air, and hence it is possible to efficiently add ions to the air.

By the way, the amount of ions per 1 $cm^3$ in the air discharged to a room was measured using the structure in which two ion generators 206 are disposed on the front walls 205a of the ducts 205 while being spaced apart from each other in the flow direction. The concentration of ions obtained as a result was approximately 10,000 per $cm^3$. Owing to this, it is possible to enhance the sterilization effect on airborne bacteria in the room, the inactivation effect on viruses, and the effect of removing odors absorbed in a curtain, clothing, etc.

Here, in this embodiment, the ducts 205 each include a laminar flow portion for causing air delivered by the rotation of the impeller 203 to flow in the form of the laminar flow, and the ion generation portions 261 and 262 are disposed in the laminar flow portion of each of the ducts 205. However, apart from that, the ion generation portions 261 and 262 may be disposed on the circular guide walls structured to cause air delivered by the rotation of the respective impellers 203 to flow in the form of the laminar flow. A position at which the ion generation portion is disposed is not particularly limited.

Further, in this embodiment, the pairs of ion generators 206 spaced apart from each other in the flow direction are disposed side by side at positions intersecting the flow direction in the two ducts 205. However, apart from that, the ion generators 206 of the two flow paths may be disposed so as to be spaced apart from each other in the flow direction.

As described above, if the apparatuses described in the respective embodiments of the present invention are placed in a room and operated continuously, positive ions and negative ions generated from the ion generators can be efficiently and evenly diffused in large quantity in the room. It is possible to widely distribute positive ions and negative ions in a room having a size of several to several tens of tatami mats, with the concentration of ions equal to or higher than 10,000 per $cm^3$. Moreover, if an appropriate apparatus type is selected from among those described in the above-mentioned embodiments depending on the size of the room, it is also possible to widely distribute positive ions and negative ions in the room, with the concentration of ions equal to or higher than 50,000 per $cm^3$.

Conventional commercially available apparatuses mounted with ion generators are capable of generating positive ions and negative ions in a room with a concentration of about 2,000 per $cm^3$ at best. In contrast, the apparatuses described in the respective embodiments of the present invention are capable of significantly increasing the concentration of ions. This has therefore enabled realizing groundbreaking effects and efficacies, which cannot be possibly achieved by the conventionally available apparatuses.

FIG. 25 shows the effects and efficacies newly realized by the technology of the present invention, in which positive ions and negative ions are distributed in a room with a high concentration. Referring to FIG. 25, an ion concentration of 2,000 per $cm^3$ has been achieved in a real space by conventional apparatuses, and removal rates of airborne viruses, airborne mold spores, and airborne mite allergens are 90%, 99%, and 23%, respectively. Note that, as for the airborne viruses, a 1-$m^3$-chamber test was performed to examine effects of an ion concentration of 7,000 per $cm^3$, and the removal rate of viruses was 99% in 10 minutes. To be precise, the other effects and efficacies shown in FIG. 25 have been unknown. In particular, it has been conceived that there is no effect on the removal of absorbed odors.

However, through experiments performed under conditions shown in FIG. 25, it has been found that, by increasing the concentration of ions, the removal rates of airborne viruses, adhering bacteria, adhering mold spores, and airborne allergens are all increased, and, in particular, an increase in concentration of ions by one order of magnitude or higher compared to the conventional concentration (2,000 per $cm^3$) provides additional effects, such as inhibition of growth of adhering bacteria and adhering mold spores and removal of absorbed odors. Further, it has been confirmed that, when the concentration of ions is made equal to or higher than 50,000 per $cm^3$, airborne avian influenza A viruses (particularly subtype H5N1) are removed 99.9% in 10 minutes, adhering bacteria (*Escherichia coli* and *Staphylococcus aureus*) are removed 99%, and absorbed sweat odor is made one level down (1/10 in terms of intensity).

With the concentration of ions in a room space which is achievable by the conventional apparatus, airborne avian influenza A viruses can be removed only up to 90% (equivalent to 73% removal in 10-minute real-space test) through a one-pass test. However, it has been demonstrated that the technology of the present invention for higher concentration can achieve a removal rate of 99% or higher in a short period of time (with an ion concentration of 50,000 per $cm^3$, 99.9% of avian influenza A viruses are removed in 10 minutes). In addition, the fact that such effects are produced against the subtype H5N1, which has been feared to have pandemic potential in recent years, suggests that the technology of the present invention for higher concentration helps prevent infection due to a new virus and is significantly beneficial in terms of public hygiene.

Further, with the concentration of ions in a real space which is achievable by the conventional apparatus, confirmed effects are limited to bacteria, allergens, and orders that are suspended in the air, and it has been predicted that there would be no effect on bacteria or the like adhering to a solid body, or that little effect could be expected thereon. However, as described below, it has been confirmed that the technology of the present invention for higher concentration is capable of removal of adhering bacteria (*Staphylococcus aureus* and *Escherichia coli*), inhibition of growth of adhering mold (*Cladosporium*), and deodorization of absorbed odors (absorbed smoke odors from cigarettes and absorbed sweat odors (isovaleric acid)) in a practical period of time.

<Deodorization Effect on Absorbed Odors>

Time periods required for the odor intensity of absorbed smoke odors from cigarettes to be made one level down were 57.5 minutes, 40 minutes, approximately 27.5 minutes, and 22.5 minutes when the concentration of ions was 7,000 per $cm^3$, 20,000 per $cm^3$, 30,000 per $cm^3$, and 50,000 per $cm^3$, respectively. As for absorbed sweat odors (isovaleric acid), the time periods required were approximately 12 hours and approximately 4 hours when the concentration of ions was 50,000 per $cm^3$ and 100,000 per $cm^3$, respectively. As can be seen from the above, the result thus obtained was that a significant deodorization effect on absorbed odors was recognized when the concentration of ions was 7,000 per $cm^3$ or higher, and that the effect was enhanced as the concentration of ions was increased.

<Adhering Mold Removing Effect>

When the concentration of ions was 30,000 per $cm^3$, the hyphal growth of *Cladosporium* became moderate (25% to 50% of test area), and when the concentration of ions was 50,000 per $cm^3$, the hyphal growth of *Cladosporium* became inconspicuous (25% or smaller in test area). As can be seen from the above, the result thus obtained was that a significant adhering mold removing effect was recognized when the concentration of ions was 30,000 per $cm^3$ or higher, and that the adhering mold removing effect was enhanced as the concentration of ions was increased.

<Adhering Bacteria Removing Effect>

When the concentration of ions was maintained at 50,000 per $cm^3$ in a refrigerator, the number of *Staphylococcus aureus* and *Escherichia coli* was reduced 99% in 7 days. As can be seen from the above, the result thus obtained was that a significant adhering bacteria removing effect was recognized when the concentration of ions was 50,000 per $cm^3$ or higher, and that the adhering bacteria removing effect was enhanced as the concentration of ions was increased.

<Airborne Virus Removing Effect>

(1) Evaluation of Infectivity of Airborne Viruses by Using Cells (Part 1)

Figure 28:
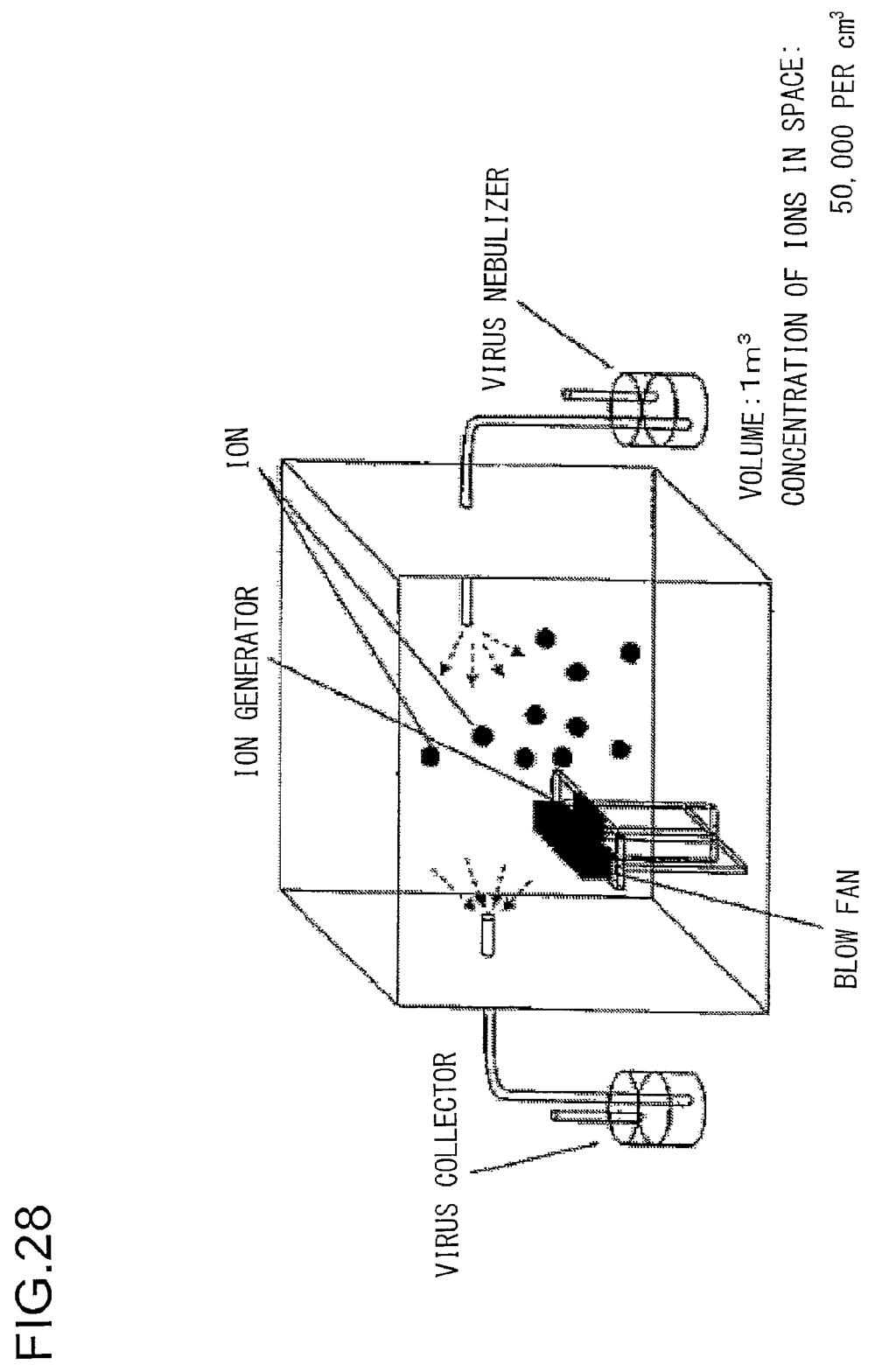
Figure 29:
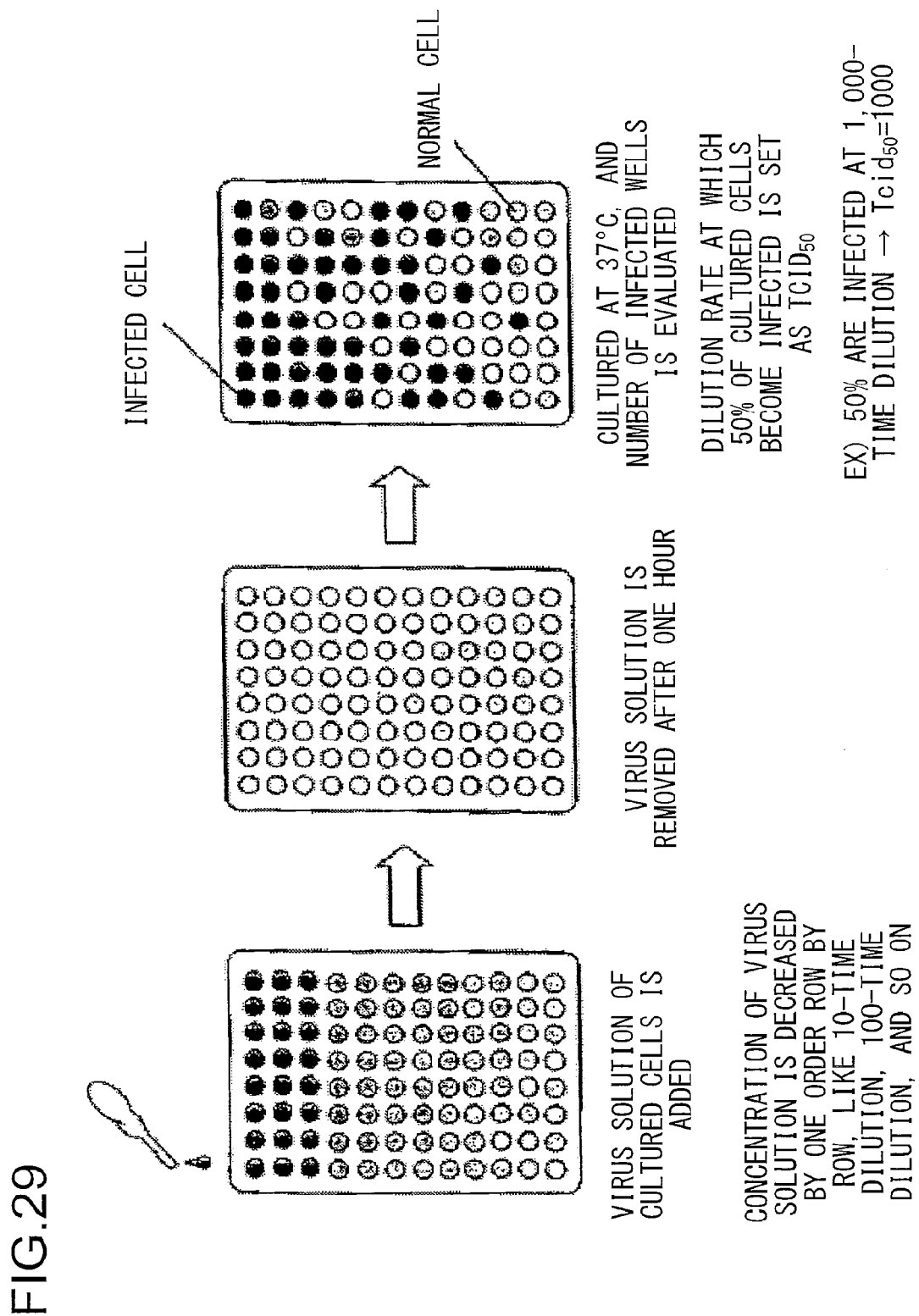
[FIG. 29] An explanatory diagram of the TCID50 method, which is a typical evaluation method for virus infectivity.

In an environment in which positive ions and negative ions are present, a verification test was conducted by using cells with the aim of verifying an infectivity reduction effect against airborne influenza viruses. As illustrated in FIG. 28, in a chamber having a volume of 1 $m^3$, the ion generator described in the embodiments and a fan for stirring the air in the chamber were set up. Subsequently, positive ions and negative ions generated from the ion generator were stirred by the fan, and the concentration of positive ions and negative ions in the air was kept even at 50,000 per $cm^3$. Then, the avian influenza A virus subtype H5N1 was sprayed into the chamber, and the airborne viruses in the chamber were retrieved through suction for 10 minutes, starting immediately after the end of the spraying and 5 minutes after the end of the spraying, respectively, to thereby examine the infectious titer of the viruses by the TCID50 method (method in which infectivity is determined by gradually inoculating cells with a diluted virus solution: see FIG. 29), which is generally used in the field of virus studies. Here, the infectious titer is an index representing the infectivity of a virus to a cell. As a result of the test, it has been confirmed that the infectious titer (infectivity) of the virus is reduced approximately 99.9% in a short period of time as short as approximately 10 minutes. Note that, when a similar experiment was conducted with an ion concentration of 7,000 per $cm^3$, the removal rate after 10 minutes was 99.0%. Further, similar experiments were conducted with the human influenza A virus subtype H1N1, and the removal rates after 25 minutes were 99.7% and approximately 99.97% when the concentration of ions was 7,000 per $cm^3$ and when the concentration of ions was 50,000 per $cm^3$, respectively. As can be seen from the above, the result thus obtained was that a significant airborne virus removing effect was recognized when the concentration of ions was 7,000 per $cm^3$ or higher, and that the airborne virus removing effect was enhanced as the concentration of ions was increased.

(2) Evaluation of Infectivity of Airborne Viruses by Using Cells (Part 2)

As illustrated in FIG. 28, in a chamber having a volume of 1 m³, the ion generator described in the embodiments of the present invention and a fan for stirring the air in the chamber were set up. Subsequently, positive ions and negative ions generated from the ion generator were stirred by the fan, and the concentration of positive ions and negative ions in the air was kept even at 50,000 per cm³. Then, the avian influenza A virus subtype H5N1 was sprayed into the chamber, and the airborne viruses in the chamber were retrieved through suction for 10 minutes, starting 5 minutes after the end of the spraying, to thereby examine changes in cells for 3 days after the cells were inoculated with the viruses. As a result, the cell inoculated with such a virus that was not subjected to the action of positive ions and negative ions was distorted and broken 3 days after the inoculation, whereas the cell inoculated with such a virus that was subjected to the action of positive ions and negative ions had little change, keeping a normal form. Owing to this fact, it has been confirmed that the action of positive ions and negative ions decreases the infectivity of a virus to a cell.

(3) Evaluation of Infectivity of Airborne Viruses by Using Small Animals

Figure 31:
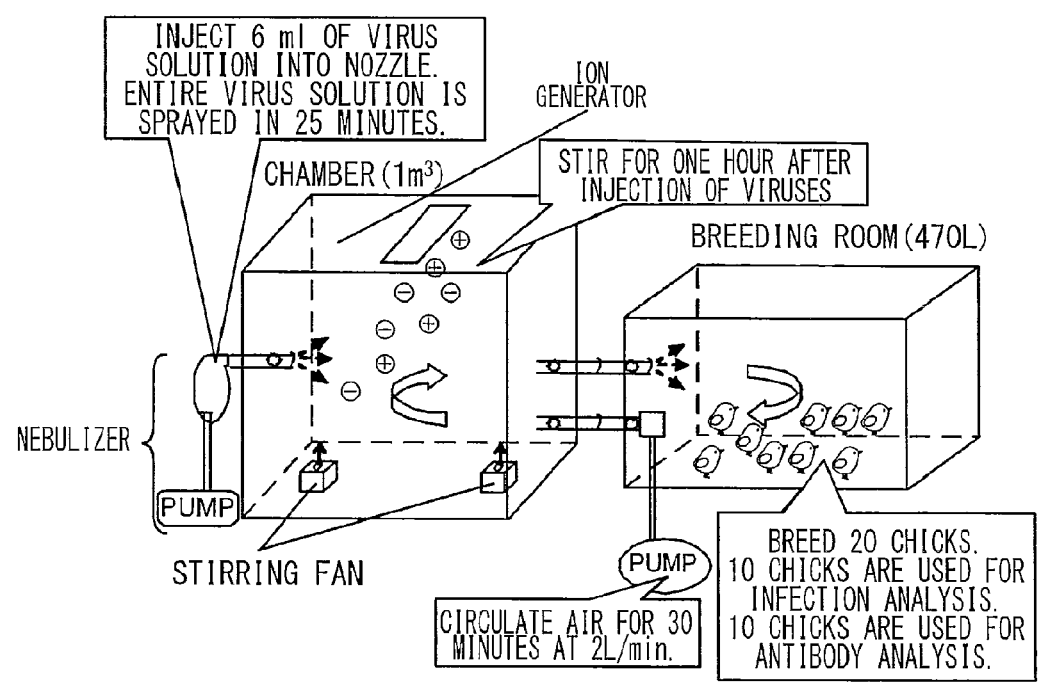

In an environment in which positive ions and negative ions are present, a verification test was conducted by using small animals (chicks) with the aim of verifying the infectivity reduction effect against airborne influenza viruses. As illustrated in FIG. 31, a chamber (room for bringing ions and viruses into contact with each other) having a volume of 1 m³, in which an ion generator and a fan for stirring air were set up, and a chick breeding room having a volume of 270 L were connected to each other with two tubes, thereby enabling the air to circulate between the chamber and the chick breeding room. Subsequently, the ventilation between the chamber and the chick breeding room was shut off, and then an influenza A virus subtype H3N2 solution having a virus concentration of $10^5$ $TCID_{50}/mL$ was all sprayed by a nebulizer over 25 minutes into chambers that were set to have even concentrations of positive ions and negative ions at 3,000 per cm³, 7,000 per cm³, 25,000 per cm³, and 50,000 per cm³, respectively (respective chambers were set as test areas 1, 2, 3, and 4). Then, for 1 hour after the spraying, positive ions and negative ions were generated from the ion generator in each of the chambers so as to maintain the above-mentioned concentration, and the ions and the viruses were stirred by the fan. For comparison, in a chamber in which the ion generator is not operated so that the concentration of ions is set to 0 (referred to as control area), the virus solution was sprayed and the stirring was performed.

After the 1-hour stirring, the shut-off between the chamber and the chick breeding room was canceled, and the air in the chamber and the air in the breeding room containing 20 chicks were circulated for 30 minutes by using a pump installed in the breeding room. After the 30-minute air circulation, the ventilation between the chamber and the chick breeding room was shut off, and the chicks were bred with only the chick breeding room capable of ventilation with outside air. After the chicks were bred for 3 days, 10 out of the 20 chicks were retrieved and dissected to collect livers, kidneys, and blood. The collected portions were analyzed by the PCR method as samples, thereby performing, for the respective portions, measurement as to whether or not the virus was present and calculating infection rates. Note that, as for the establishment of infection, if the virus is present in any one of the above-mentioned three portions, it is considered that the infection has been established. After the chicks were bred for 18 days more (21 days after the virus spraying), the remaining 10 chicks were retrieved to collect blood, and antibody analysis was conducted utilizing hemagglutination inhibition, to thereby calculate antibody prevalence rates.

In order to determine whether or not there is virus infection in the above-mentioned test, the evaluation was performed using two indicators: (a) the infection rate (rate of chicks that have viruses invading living bodies); and (b) the antibody prevalence rate (rate of chicks that have immunity because of biological defense reaction caused by invasion of viruses to living bodies). The results are shown in Table 1 and FIG. 30.

TABLE 1

|  | Control area | Test area 1 | Test area 2 | Test area 3 | Test area 4 |
|---|---|---|---|---|---|
| Ion concentration (per cm³) | 0 | 3,000 | 7,000 | 25,000 | 50,000 |
| Infection rate (%) | 70 | 30 | 20 | 20 | 10 |
| Antibody prevalence rate (%) | 90 | 40 | 30 | 30 | 30 |

Figure 30:
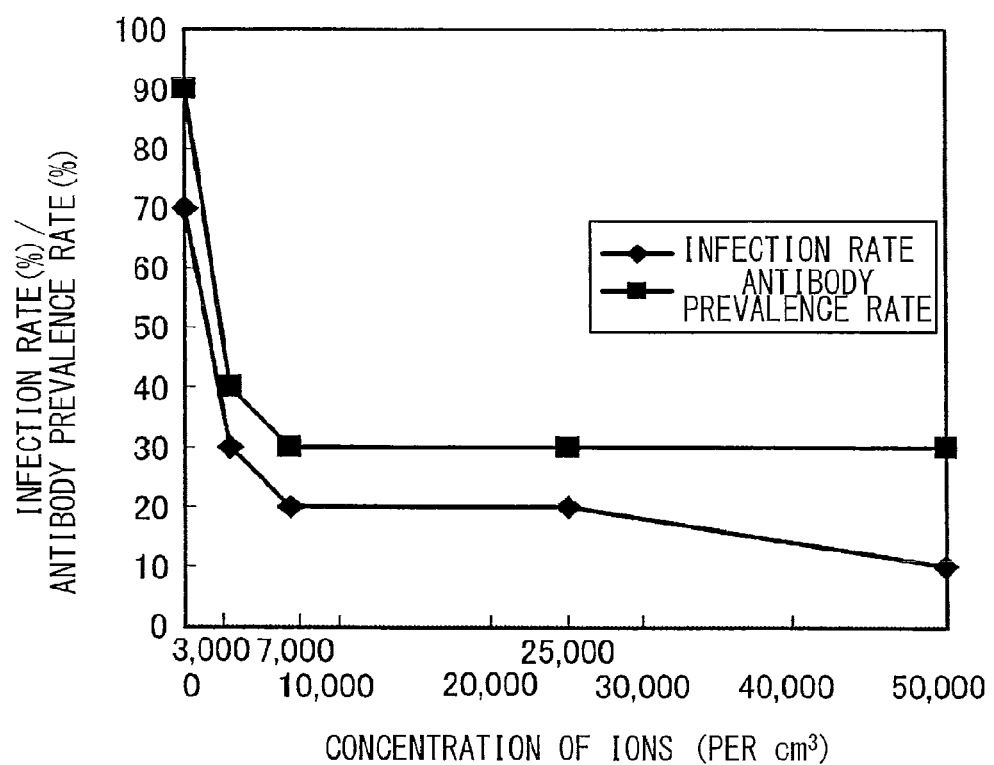
[FIG. 30] A graph showing relation between the concentration of positive ions and negative ions and an infection rate/antibody prevalence rate of chicks, which was obtained through a test of FIG. 31.

From the results of Table 1 and FIG. 30, it has been confirmed that, in an environment in which the concentration of ions is 3,000 per cm³, the infection rate is decreased from 70% to 30%, and the antibody prevalence rate is decreased from 90% to 40%, and that, in an environment in which the concentration of ions is 7,000 per cm³, the infection rate is decreased from 70% to 20%, and the antibody prevalence rate is decreased from 90% to 30%. In other words, it has been found that, by treating the influenza A virus subtype H3N2 for 1 hour with positive ions and negative ions, it is possible to significantly decrease the infectivity of the viruses to the chicks.

Figure 32:
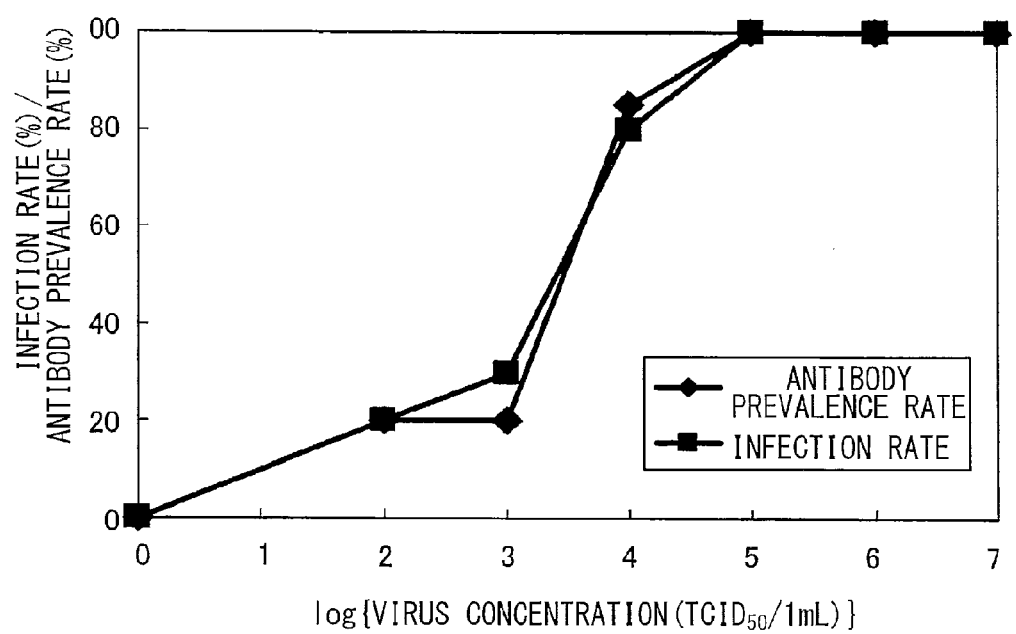
[FIG. 32] A graph showing an example of relation between a virus concentration and an infection rate of chicks.

Further, based on the fact that, in the environment in which the concentration of ions is 7,000 per cm³, a 50% decrease and a 60% decrease were achieved for the infection rate and the antibody prevalence rate, respectively, it is conceivable that 90 to 99% of the influenza viruses were inactivated, referring to a graph of infection rate/antibody prevalence rate with respect to the concentration of influenza viruses, which was obtained by an infection rate test (see FIG. 32).

Here, in the test of the present invention, as illustrated in FIG. 32, the test was conducted using the virus solution having the virus concentration of $10^5$ $TCID_{50}/mL$, with which 100% of the chicks were found to have infection through the infection rate test. However, taking into consideration the fact that the infection rate and the antibody prevalence rate were 70% and 90% in the control area, respectively, it is conceivable that the chicks used for the test of the present invention (Table 1 and FIG. 30) were such a lot that had slightly stronger resistance to the viruses compared to the lot of chicks used for the infection rate test (FIG. 32).

Industrial Applicability

The present invention relates to a method of providing a highly-purified room, and application of the present invention to such a place that an indefinite number of people gather or come and go helps prevent infection due to pathogenic viruses, and is thus significantly beneficial for the public hygiene. Further, it is obvious that the space purified according to the present invention can be used to a sufficient extent for growing livestock and plants including mushrooms (so-called sterile growing).

| Reference Signs List | |
|---|---|
| 1 | ion diffusing apparatus |
| 2 | housing |
| 3 | suction opening |
| 4 | air filter |
| 5 | blower |
| 6 | duct (flow path) |
| 6a, 6b | curved surface portion |
| 7 | vertical-widening portion |
| 8 | lateral-widening portion |
| 8a to 8h | laterally-separated path |
| 10 | opening portion |
| 10a to 10d | blowout opening |
| 11 to 14 | vertically-separated path |
| 17 | first ion generator |
| 17A | positive ion generation portion |
| 17B | negative ion generation portion |
| 18 | second ion generator |
| 18A | positive ion generation portion |
| 18B | negative ion generation portion |
| 19 | holding member |
| 100 | air purifying apparatus |
| 101 | housing |
| 111 | suction opening |
| 112 | blowout opening |
| 102 | blower |
| 121 | impeller |
| 122 | casing |
| 122a | circular guide wall |
| 122b | air outlet |
| 103 | filter |
| 104 | duct |
| 105 | ion generator |
| 151 | positive ion generation portion |
| 152 | negative ion generation portion |
| 153 | holding member |
| 200 | ion emitting apparatus |
| 202 | motor |
| 221 | output shaft |
| 203 | impeller (blower) |
| 204 | casing (wind aligning member) |
| 241 | circular guide wall |
| 242 | air outlet |
| 205 | duct (flow path, cylindrical portion) |
| 206 | ion generator |
| 261 | positive ion generation portion |
| 262 | negative ion generation portion |
| 263 | holding member |
| 207 | wind direction member |
| 272 | wind direction portion |

The invention claimed is:

1. A method of purifying an inside of a room, comprising operating an ion diffusing apparatus so as to deliver an air current from the blowout opening in a substantially horizontal direction so that an upper portion of the air current flows with a higher blowout speed compared to a blowout speed of a lower portion of the air current in order to widely distribute, with a high concentration, positive ions and negative ions in a room or a work space, whereby a pathogenic effect is removed from an airborne microorganism and/or an adhering microorganism, the ion diffusing apparatus comprising:

an ion generator having, a positive ion generation portion for generating positive ions each comprising $H^+(H_2O)_m$, where m is an arbitrary integer, and a negative ion generation portion for generating negative ions each comprising $O_2^-(H_2O)_n$, where n is an arbitrary integer;

a blower for delivering the positive ions and the negative ions, which are generated from the ion generator, from a blowout opening;

a duct connecting between the blowout opening and the blower;

a plurality of vertically-separated paths formed inside the duct by dividing an interior of the duct in a vertical direction; and laterally-separated paths formed inside the duct by further dividing the vertically-separated paths, wherein the positive ion generation portion and the negative ion generation portion are disposed in such orientations as to be spaced apart from each other in a direction intersecting a flow direction such that the positive ions generated by the positive ion generation portion flow through one of a pair of neighboring paths among the laterally-separated paths and the negative ions generated by the negative ion generation portion flow through the other of the neighboring paths.

2. A method of purifying an inside of a room according to claim 1, wherein a concentration of the positive ions and the negative ions in air of the inside of the room is set to 7,000 per $cm^3$ or higher.

3. A method of purifying an inside of a room according to claim 1, wherein a concentration of the positive ions and the negative ions in air of the inside of the room is set to 30,000 per $cm^3$ or higher.

4. A method of purifying an inside of a room according to claim 1, wherein a concentration of the positive ions and the negative ions in air of the inside of the room is set to 50,000 per $cm^3$ or higher.

5. A method of purifying an inside of a room according to claim 1 comprising a sectioning portion for sectioning between the positive ion generation portion and the negative ion generation portion along an air current.

6. A method of purifying an inside of a room according to claim 5, wherein a generation amount of the positive ions generated from the positive ion generation portion and a generation amount of the negative ions generated from the negative ion generation portion are each 1.5 million per $cm^3$ or higher at a position distanced 50 cm from the positive ion generation portion and the negative ion generation portion.

7. A method of purifying an inside of a room according to claim 1, wherein a generation amount of the positive ions generated from the positive ion generation portion and a generation amount of the negative ions generated from the negative ion generation portion are each 1.5 million per $cm^3$ or higher at a position distanced 50 cm from the positive ion generation portion and the negative ion generation portion.

* * * * *